United States Patent
Kawashima et al.

(10) Patent No.: US 7,897,774 B2
(45) Date of Patent: Mar. 1, 2011

(54) CYCLIC COMPOUND HAVING QUINOLYLALKYLTHIO GROUP

(75) Inventors: Kenji Kawashima, Ikoma (JP); Takahiro Honda, Ikoma (JP); Hisashi Tajima, Ikoma (JP); Kazuyoshi Okamoto, Ikoma (JP); Minoru Yamamoto, Ikoma (JP)

(73) Assignee: Santen Pharmaceutical Co., Ltd., Osaka-shi, Osaka (JP)

( * ) Notice: Subject to any disclaimer, the term of this patent is extended or adjusted under 35 U.S.C. 154(b) by 805 days.

(21) Appl. No.: 11/897,308

(22) Filed: Aug. 30, 2007

(65) Prior Publication Data

US 2008/0021064 A1 Jan. 24, 2008

Related U.S. Application Data

(63) Continuation of application No. PCT/JP2006/304055, filed on Mar. 3, 2006.

(30) Foreign Application Priority Data

Mar. 3, 2005 (JP) ............................. 2005-058270

(51) Int. Cl.
C07D 215/38 (2006.01)
(52) U.S. Cl. ...................... 546/159; 546/162
(58) Field of Classification Search ............... 546/159, 546/162; 514/312
See application file for complete search history.

(56) References Cited

U.S. PATENT DOCUMENTS

| | | | |
|---|---|---|---|
| 6,008,230 A | 12/1999 | Oku et al. | |
| 6,051,593 A | 4/2000 | Tang et al. | |
| 6,114,371 A | 9/2000 | Tang et al. | |
| 6,130,238 A | 10/2000 | Tang et al. | |
| 6,133,305 A | 10/2000 | Tang et al. | |
| 6,258,812 B1 | 7/2001 | Bold et al. | |
| 6,262,112 B1 | 7/2001 | Mittendorf et al. | |
| 6,313,158 B1 | 11/2001 | Tang et al. | |
| 6,316,429 B1 | 11/2001 | Tang et al. | |
| 6,350,754 B2 | 2/2002 | Tang et al. | |
| 6,486,185 B1 | 11/2002 | McMahon et al. | |
| 6,506,763 B2 | 1/2003 | Tang et al. | |
| 6,514,974 B2 | 2/2003 | Bold et al. | |
| 6,573,278 B2 | 6/2003 | Mittendorf et al. | |
| 6,579,897 B2 | 6/2003 | Tang et al. | |
| 6,624,174 B2 | 9/2003 | Manley et al. | |
| 6,683,082 B2 | 1/2004 | Tang et al. | |
| 6,696,448 B2 | 2/2004 | Tang et al. | |
| 6,696,463 B2 | 2/2004 | Tang et al. | |
| 6,710,047 B2 | 3/2004 | Bold et al. | |
| 6,849,641 B1 | 2/2005 | Tang et al. | |
| 6,987,113 B2 | 1/2006 | Tang et al. | |

| | | |
|---|---|---|
| 7,122,547 B1 | 10/2006 | Huth et al. |

FOREIGN PATENT DOCUMENTS

| | | |
|---|---|---|
| EP | 1 602 647 A1 | 12/2005 |
| JP | 10-505600 A | 6/1998 |
| JP | 11-514361 A | 12/1999 |
| JP | 2002-511852 A | 4/2001 |
| JP | 2001-508800 A | 7/2001 |
| JP | 2001-515470 A | 9/2001 |
| JP | 2002-529452 A | 9/2002 |
| JP | 2003-520853 A | 7/2003 |
| WO | WO 96/09294 A1 | 3/1996 |

(Continued)

OTHER PUBLICATIONS

Siegfried H. Reich, Michael Melnick, Mark J. Pino et al., "Structure-based design and synthesis of substituted 2-butanols as nonpeptidic inhibitors of HIV protease secondary amine series," *J. Med. Chem.*, vol. 39, 1996, pp. 2781 to 2794, XP002557981.
Supplementary European Search Report dated Nov. 30, 2009 for European application EP 06 71 5138.1.

(Continued)

*Primary Examiner*—D. Margaret Seaman
(74) *Attorney, Agent, or Firm*—Holtz, Holtz, Goodman & Chick, P.C.

(57) ABSTRACT

The present invention relates to a synthesis study of novel cyclic compounds having a quinolylalkylthio group represented by the formula (1), and pharmacological actions of the compounds.

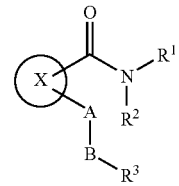

(1)

In the formula, the ring X represents:

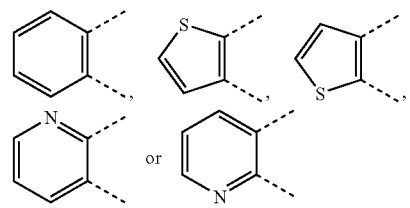

which may have halogen and/or alkyl; $R^1$ and $R^2$ independently represent hydrogen, alkyl, cycloalkyl, aryl or a (non) aromatic heterocycle; $R^3$ represents qinolyl; A represents sulfur, sulfinyl or sulfonyl; and B represents alkylene.

6 Claims, No Drawings

FOREIGN PATENT DOCUMENTS

| | | | |
|---|---|---|---|
| WO | WO 97/30035 | A1 | 8/1997 |
| WO | WO 98/35958 | A1 | 8/1998 |
| WO | WO 98/37061 | A1 | 8/1998 |
| WO | WO 98/50356 | A1 | 11/1998 |
| WO | WO 00/27819 | A2 | 5/2000 |
| WO | WO 01/55114 | A1 | 8/2001 |
| WO | WO 02/062766 | A | 8/2002 |
| WO | WO 2004-078723 | A1 | 9/2004 |
| WO | 2008093677 | * | 8/2008 |

OTHER PUBLICATIONS

Carroll F. Ivy et al., "Synthesis of Some 4-Substituted 8-Amino-6-Methoxyquinolines as Potential Antimalarials," *Journal of Medicinal Chemsitry*, 1979, vol. 22, No. 6, pp. 694 to 699.

Messinger Paul et al., "Sulfones as Chemical Carriers of Substances with Germicidal Activity. VIII: Sulfonyl Derivatives of the Mannich Bases of Quinaldine, Pyrrole and Phenol," *Archiv der Pharmazie*, 1977, vol. 310, No. 3, pp. 249 to 255.

Buchmann Gerhard, "2-Vinylquinoline. I. Addition Reactions at the C-C Double Bond of 2-Vinyl Quinoline," *Chemical Abstracts*, 1964, vol. 61, 11969a-c.

Molecular Medicine, vol. 35, special issue, "Molecular Mechanism of Symptoms and Pathologic Conditions," Nakayama Shoten, 73-74, (1998).

Protein, Nucleic Acid, Enzyme, extra number, "The Most Advanced Development of New Drugs," Kyoritsu Shuppan, 1182-1187, (2000).

* cited by examiner

CYCLIC COMPOUND HAVING QUINOLYLALKYLTHIO GROUP

This is a Continuation-in-Part Application of International Application No. PCT/JP2006/304055 (not published in English) filed Mar. 3, 2006, which is incorporated herein by reference in its entirety.

TECHNICAL FIELD

The present invention relates to a novel cyclic compound having a quinolylalkylthio group or a salt thereof useful as a pharmaceutical. Such a compound is useful as a therapeutic agent for a disease associated with angiogenesis, particularly as a therapeutic agent for cancer, rheumatoid arthritis, age-related macular degeneration, diabetic retinopathy, retinopathy of prematurity, retinal vein occlusion, polypoid choroidal angiopathy, diabetic macular edema, psoriasis vulgaris, atherosclerosis or the like.

BACKGROUND ART

Angiogenesis is a phenomenon in which a new vascular network is formed from an existing blood vessel and is observed mainly in a microvessel. Angiogenesis is originally a physiological phenomenon and is essential for blood vessel formation in fetal life, but it is usually observed only at a limited site such as endometrium or follicle or at a limited period such as a wound healing process in adults. However, pathological angiogenesis is observed in a disease such as cancer, rheumatoid arthritis, age-related macular degeneration, diabetic retinopathy, retinopathy of prematurity, retinal vein occlusion, polypoid choroidal angiopathy, diabetic macular edema, psoriasis vulgaris or atherosclerosis, and closely relates to the progress of pathological conditions of these diseases. It is considered that angiogenesis is regulated by balance between its promoting factor and inhibitory factor, and angiogenesis is caused by disruption of the balance (see Molecular Medicine vol. 35, special issue, "Molecular Mechanism of Symptoms and Pathological conditions", Nakayama Syoten, 73-74 (1998), and Protein, Nucleic Acid and Enzyme, extra number, "The Most Advanced Development of New Drugs", Kyoritsu Shuppan, 1182-1187 (2000)).

A vascular endothelial growth factor (hereinafter abbreviated as "VEGF") is a factor which specifically acts on a receptor (Flt-1, KDR/Flk-1 or the like) present on the surface of vascular endothelial cells, thereby to promote proliferation and migration of the vascular endothelial cells, construction of a capillary vessel network due to vasculogenesis, and plays a very important role in incidence of angiogenesis. Accordingly, there have been many reports on attempts to treat a disease associated with angiogenesis by inhibiting VEGF to control the incidence of angiogenesis. Examples of drugs to be used for the treatment include indolin-2-one derivatives (see WO 98/50356), phthalazine derivatives (see WO 98/35958), quinazoline derivatives (see WO 97/30035), anthranilic acid amide derivatives (see WO 00/27819), 2-aminonicotinic acid derivatives (see WO 01/55114), 4-pyridylalkylthio derivatives (see WO 04/078723) and the like.

However, there is no description on cyclic compounds having a quinolylalkylthio group in these Patent publications.

On the other hand, compounds having a chemical structure relatively close to those of cyclic compounds having a quinolylalkylthio group are reported in WO 98/37061 and WO 96/09294. The former relates to arylsulfonamide derivatives and discloses a therapeutic effect on neurodegenerative diseases as its application. Further, the latter relates to substituted heterocyclic compounds and discloses an inhibitory effect on p56lck protein-tyrosine kinase as its application. However, both of these Patent publications disclose only enormous combinations of chemical structures, and do not make specific disclosure of cyclic compounds having a quinolylalkylthio group at all.

DISCLOSURE OF THE INVENTION

Problems to be Solved

It is a very interesting subject to study synthesis of novel cyclic compounds having a quinolylalkylthio group and to find pharmacological actions of the compounds.

Means of Solving Problems

The present inventors have studied synthesis of cyclic compounds having a quinolylalkylthio group and succeeded in producing a large number of novel compounds.

Further, they studied pharmacological actions of these compounds widely, and found that these compounds have an antiangiogenic effect, and are useful as a therapeutic agent for a disease associated with angiogenesis, particularly as a therapeutic agent for cancer, rheumatoid arthritis, age-related macular degeneration, diabetic retinopathy, retinopathy of prematurity, retinal vein occlusion, polypoid choroidal angiopathy, diabetic macular edema, psoriasis vulgaris, atherosclerosis or the like, thus accomplished the present invention.

Advantage of the Invention

The present invention provides a novel cyclic compound having a quinolylalkylthio group or a salt thereof useful as a pharmaceutical. The novel cyclic compound according to the present invention has an excellent antiangiogenic effect, and is useful as a therapeutic agent for a disease associated with angiogenesis, for example, cancer, rheumatoid arthritis, age-related macular degeneration, diabetic retinopathy, retinopathy of prematurity, retinal vein occlusion, polypoid choroidal angiopathy, diabetic macular edema, psoriasis vulgaris, atherosclerosis or the like.

BEST MODE FOR CARRYING OUT THE INVENTION

The present invention relates to a compound represented by the general formula (1) or a salt thereof (hereinafter referred to as "the compound of the present invention" unless otherwise specified) and a pharmaceutical composition containing the compound of the present invention. Describing a pharmaceutical use of the compound of the present invention more specifically, it relates to a therapeutic agent for a disease associated with angiogenesis containing the compound of the present invention as an active ingredient, and for example, it relates to a therapeutic agent for cancer, rheumatoid arthritis, age-related macular degeneration, diabetic retinopathy, retinopathy of prematurity, retinal vein occlusion, polypoid choroidal angiopathy, diabetic macular edema, psoriasis vulgaris, atherosclerosis or the like.

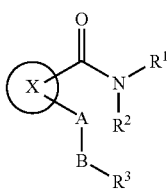

(1)

[In the formula, the ring X represents:

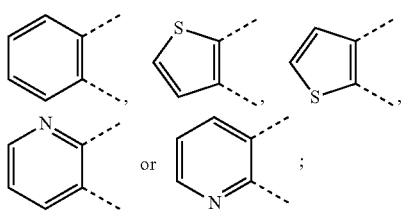

which may have one or plural substituents selected from a halogen atom and an alkyl group;

$R^1$ and $R^2$ may be the same or different and each represents a hydrogen atom, an alkyl group, a cycloalkyl group, an aryl group, an aromatic heterocyclic group or a nonaromatic heterocyclic group;

in the case where $R^1$ or $R^2$ is an alkyl group, the alkyl group may have one or plural substituents selected from an aryl group, a halogenoaryl group and an alkoxyaryl group;

in the case where $R^1$ or $R^2$ is an aryl group, the aryl group may have one or plural substituents selected from a halogen atom, a hydroxy group, an alkoxy group, a halogenoalkoxy group, an aryloxy group, an alkyl group, a halogenoalkyl group, an alkenyl group, an alkynyl group, a cycloalkyl group, an aryl group, an amino group, an alkylamino group, an arylamino group, a mercapto group, an alkylthio group, an arylthio group, an alkylcarbonyl group, an arylcarbonyl group and a nitro group;

$R^1$ and $R^2$ may be combined together to form a nonaromatic heterocycle;

$R^3$ represents a quinolyl group, the quinolyl group may have one or plural substituents selected from a halogen atom, a hydroxy group, an alkoxy group, an aryloxy group, an alkyl group and an aryl group, and a nitrogen atom of the quinolyl group may be coordinated with an oxo ligand;

A represents a sulfur atom, a sulfinyl group or a sulfonyl group; and

B represents an alkylene group.

Hereinafter the same definitions shall apply.]

The respective groups as used in the claims and specification have the following meanings throughout the claims and specification.

The "halogen atom" refers to fluorine, chlorine, bromine or iodine.

The "alkyl" refers to straight-chain or branched alkyl having 1 to 6 carbon atoms. Specific examples thereof include methyl, ethyl, n-propyl, n-butyl, n-pentyl, n-hexyl, isopropyl, isobutyl, sec-butyl, tert-butyl, isopentyl and the like.

The "cycloalkyl" refers to cycloalkyl having 3 to 8 carbon atoms. Specific examples thereof include cyclopropyl, cyclobutyl, cyclopentyl, cyclohexyl, cycloheptyl, cyclooctyl and the like.

The "aryl" refers to monocyclic aromatic hydrocarbon, or bicyclic or tricyclic condensed polycyclic aromatic hydrocarbon having 6 to 14 carbon atoms. Further, condensed polycyclic hydrocarbon formed by condensation of such monocyclic aromatic hydrocarbon, or bicyclic or tricyclic condensed polycyclic aromatic hydrocarbon with a cycloalkane ring is also included in the "aryl" of the present invention. Specific examples of the monocyclic aromatic hydrocarbon include phenyl, and specific examples of the condensed polycyclic aromatic hydrocarbon include naphthyl, anthryl, phenanthryl and the like, and specific examples of the condensed polycyclic hydrocarbon include indanyl, tetrahydronaphthyl, tetrahydroanthryl and the like.

The "aromatic heterocycle" refers to a monocyclic aromatic heterocycle, or a bicyclic or tricyclic condensed polycyclic aromatic heterocycle having one or plural heteroatoms (a nitrogen atom, an oxygen atom or a sulfur atom) in the ring.

Specific examples of the monocyclic aromatic heterocycle include aromatic heterocycles having one heteroatom in the ring such as pyrrole, furan, thiophene and pyridine; azole aromatic heterocycles such as imidazole, oxazole, thiazole, pyrazole, isoxazole and isothiazole; aromatic heterocycles having two nitrogen atoms in the ring such as pyrazine and pyrimidine, and the like. Specific examples of the bicyclic or tricyclic condensed polycyclic aromatic heterocycle include condensed aromatic heterocycles such as indole, isoindole, benzoimidazole, benzoxazole, benzothiazole, quinoline, isoquinoline, thianthrene, phenoxathiin and phenanthroline, and the like.

The "nonaromatic heterocycle" refers to a monocyclic nonaromatic heterocycle, or a bicyclic or tricyclic condensed polycyclic nonaromatic heterocycle having one or plural heteroatoms (a nitrogen atom, an oxygen atom or a sulfur atom) in the ring.

Specific examples of the monocyclic nonaromatic heterocycle include saturated nonaromatic heterocycles having one heteroatom in the ring such as pyrrolidine, tetrahydrofuran, tetrahydrothiophene, piperidine, tetrahydropyran and homopiperazine; saturated nonaromatic heterocycles having two heteroatoms in the ring such as imidazolidine, oxazolidine, thiazolidine, pyrazolidine, piperazine, morpholine, thiomorpholine, homopiperidine and homomorpholine; unsaturated nonaromatic heterocycles having one heteroatom in the ring such as pyrroline, dihydrofuran, dihydrothiophene, tetrahydropyridine, dihydropyridine, dihydropyran and pyran; unsaturated nonaromatic heterocycles having two heteroatoms such as imidazoline, oxazoline, thiazoline and pyrazoline, and the like. Specific examples of the bicyclic or tricyclic condensed polycyclic nonaromatic heterocycle include chroman, indoline, isoindoline, xanthine and the like.

The "alkoxy" refers to straight-chain or branched alkoxy having 1 to 6 carbon atoms. Specific examples thereof include methoxy, ethoxy, n-propoxy, n-butoxy, n-pentoxy, n-hexyloxy, isopropoxy, isobutoxy, sec-butoxy, tert-butoxy, isopentoxy and the like.

The "aryloxy" refers to monocyclic aromatic hydrocarbonoxy, or bicyclic or tricyclic condensed polycyclic aromatic hydrocarbonoxy having 6 to 14 carbon atoms. Specific examples of the monocyclic aromatic hydrocarbonoxy include phenoxy, and specific examples of the condensed polycyclic aromatic hydrocarbonoxy include naphthyloxy, anthryloxy, phenanthryloxy and the like.

The "alkenyl" refers to straight-chain or branched alkenyl having 2 to 8 carbon atoms. Specific examples thereof include vinyl, allyl, 1-propenyl, 3-butenyl, 3-pentenyl, 4-hexenyl, 5-heptenyl, 7-octenyl, 1-methylvinyl and the like.

The "alkynyl" refers to straight-chain or branched alkynyl having 2 to 8 carbon atoms. Specific examples thereof include ethynyl, 2-propynyl, 2-butynyl, 3-pentynyl, 4-hexynyl, 5-heptynyl, 7-octynyl, 2-methylbutynyl and the like.

The "alkylamino" refers to monoalkylamino having 1 to 6 carbon atoms or dialkylamino having 2 to 12 carbon atoms. Specific examples of the monoalkylamino include methylamino, ethylamino, hexylamino and the like, and specific examples of the dialkylamino include ethylmethylamino, dimethylamino, diethylamino, dihexylamino and the like.

The "arylamino" refers to monoarylamino having 6 to 20 carbon atoms or diarylamino having 12 to 28 carbon atoms. Specific examples of the monoarylamino include phenylamino, naphthylamino, ethylphenylamino and the like, and specific examples of the diarylamino include diphenylamino, dianthrylamino and the like.

The "alkylthio" refers to straight-chain or branched alkylthio having 1 to 6 carbon atoms. Specific examples thereof include methylthio, ethylthio, n-propylthio, n-butylthio, n-pentylthio, n-hexylthio, isopropylthio, isobutylthio, sec-butylthio, tert-butylthio, isopentylthio and the like.

The "arylthio" refers to monocyclic aromatic hydrocarbonthio, or bicyclic or tricyclic condensed polycyclic aromatic hydrocarbonthio having 6 to 14 carbon atoms. Specific examples of the monocyclic aromatic hydrocarbonthio include phenylthio, and specific examples of the condensed polycyclic aromatic hydrocarbonthio include naphthylthio, anthrylthio, phenanthrylthio and the like.

The "alkylcarbonyl" refers to straight-chain or branched alkylcarbonyl having 2 to 7 carbon atoms. Specific examples thereof include methylcarbonyl, ethylcarbonyl, n-propylcarbonyl, n-butylcarbonyl, n-pentylcarbonyl, n-hexylcarbonyl, isopropylcarbonyl, isobutylcarbonyl, sec-butylcarbonyl, tert-butylcarbonyl, isopentylcarbonyl and the like.

The "arylcarbonyl" refers to monocyclic aromatic hydrocarboncarbonyl, or bicyclic or tricyclic condensed polycyclic aromatic hydrocarboncarbonyl having 7 to 15 carbon atoms. Specific examples thereof include phenylcarbonyl, naphthylcarbonyl, anthrylcarbonyl, phenanthrylcarbonyl and the like.

The "alkylene" refers to straight-chain or branched alkylene having 1 to 6 carbon atoms. Specific examples thereof include methylene, ethylene, trimethylene, tetramethylene, pentamethylene, hexamethylene, methylmethylene, dimethylmethylene, propylene, 2-methyltrimethylene and the like.

The "halogenoalkoxy" refers to alkoxy having one or plural of the same or different halogen atoms as substituents.

The "halogenoalkyl" refers to alkyl having one or plural of the same or different halogen atoms as substituents.

The "halogenoaryl" refers to aryl having one or plural of the same or different halogen atoms as substituents.

The "alkoxyaryl" refers to aryl having one or plural of the same or different alkoxy groups as substituents.

When the compound of the present invention has a free hydroxy group, amino group, alkylamino group, arylamino group or mercapto group as a substituent, these substituents may be protected with a protecting group. Further, when the aromatic heterocyclic group or the nonaromatic heterocycle has a free nitrogen atom, the nitrogen atom may also be protected with a protecting group.

The "protecting group for a free hydroxy group" refers to a group widely used as a protecting group for a free hydroxy group including a substituted or unsubstituted alkyl group, or an unsubstituted alkenyl group such as a methyl group, a methoxymethyl group, a benzyl group, a 4-methoxyphenylmethyl group or an allyl group; a substituted or unsubstituted nonaromatic heterocyclic group such as a 3-bromotetrahydropyranyl group, a tetrahydropyranyl group or a tetrahydrofuranyl group; a substituted or unsubstituted alkylcarbonyl group or a substituted or unsubstituted arylcarbonyl group such as an acetyl group, a trifluoroacetyl group, a benzoyl group or a 4-chlorobenzoyl group; a substituted or unsubstituted alkyloxycarbonyl group, an unsubstituted alkenyloxycarbonyl group, or a substituted or unsubstituted aryloxycarbonyl group such as a methoxycarbonyl group, an ethoxycarbonyl group, an isobutoxycarbonyl group, a tert-butoxycarbonyl group, a benzyloxycarbonyl group, a p-methoxybenzyloxycarbonyl group, a 9-fluorenylmethoxycarbonyl group, a vinyloxycarbonyl group, an aryloxycarbonyl group, a phenyloxycarbonyl group or a p-nitrophenyloxycarbonyl group; a substituted silyl group such as a trimethylsilyl group, a triethylsilyl group, a triisopropylsilyl group, a tert-butyldimethylsilyl group or a tert-butyldiphenylsilyl group, and the like.

The "protecting group for a free amino group, a free alkylamino group, a free arylamino group, an aromatic heterocyclic group having a free nitrogen atom, or a nonaromatic heterocyclic group having a free nitrogen atom" refers to a group widely used as a protecting group for a free amino group, a free alkylamino group, a free arylamino group, an aromatic heterocyclic group having a free nitrogen atom, or a nonaromatic heterocyclic group having a free nitrogen atom including an unsubstituted alkenyl group such as an allyl group; a hydrocarbonyl group such as a formyl group; a substituted or unsubstituted alkylcarbonyl group, a substituted or unsubstituted arylcarbonyl group, or an unsubstituted aromatic heterocyclic carbonyl group such as an acetyl group, a trichloroacetyl group, a trifluoroacetyl group, a benzoyl group, a 4-chlorobenzoyl group or a picolinoyl group; a substituted or unsubstituted alkyloxycarbonyl group, or a substituted or unsubstituted aryloxycarbonyl group such as a methoxycarbonyl group, an isobutoxycarbonyl group, a tert-butoxycarbonyl group, a 2,2,2-trichloroethoxycarbonyl group, a benzyloxycarbonyl group, a diphenylmethoxycarbonyl group, a phenoxycarbonyl group or a m-nitrophenoxycarbonyl group; a substituted or unsubstituted alkylsulfonyl group, or a substituted or unsubstituted arylsulfonyl group such as a methylsulfonyl group, a benzylsulfonyl group, a phenylsulfonyl group, a 4-chlorophenylsulfonyl group, a tolylsulfonyl group or a 2,4,6-trimethylphenylsulfonyl group, and the like.

The "protecting group for a free mercapto group" refers to a group widely used as a protecting group for a free mercapto group including a substituted or unsubstituted alkyl group, or an unsubstituted alkenyl group such as a methyl group, a methoxymethyl group, a benzyl group, a 4-methoxyphenylmethyl group or an allyl group; a substituted or unsubstituted nonaromatic heterocyclic group such as a 3-bromotetrahydropyranyl group, a tetrahydropyranyl group or a tetrahydrofuranyl group; a substituted or unsubstituted alkylcarbonyl group, or a substituted or unsubstituted arylcarbonyl group such as an acetyl group, a trifluoroacetyl group, a benzoyl group or a 4-chlorobenzoyl group; a substituted or unsubstituted alkyloxycarbonyl group, an unsubstituted alkenyloxycarbonyl group, or a substituted or unsubstituted aryloxycarbonyl group such as a methoxycarbonyl group, an ethoxycarbonyl group, an isobutoxycarbonyl group, a tert-butoxycarbonyl group, a benzyloxycarbonyl group, a p-methoxybenzyloxycarbonyl group, a 9-fluorenylmethoxycarbonyl group, a vinyloxycarbonyl group, an aryloxycarbonyl group, a phenyloxycarbonyl group or a p-nitrophenyloxycarbonyl group, and the like.

The above-mentioned substituted alkyl group, substituted nonaromatic heterocyclic group, substituted alkylcarbonyl group, substituted arylcarbonyl group, substituted alkyloxycarbonyl group, substituted aryloxycarbonyl group, substituted silyl group, substituted alkylsulfonyl group and substituted arylsulfonyl group refer to an alkyl group, a nonaromatic heterocyclic group, an alkylcarbonyl group, an arylcarbonyl group, an alkyloxycarbonyl group, an aryloxycarbonyl group, a silyl group, an alkylsulfonyl group and an arylsulfonyl group substituted with one or plural groups selected from a halogen atom, an alkoxy group, an alkyl group, an aryl group, a halogenoaryl group, an alkoxyaryl group and a nitro group, respectively.

The "plural groups" as used herein may be the same or different from one another and refer to preferably 2 or 3 groups, and more preferably 2 groups.

Further, in the "group" as used herein, a hydrogen atom, a halogen atom and an oxo ligand are also included.

The "salt" of the compound of the present invention is not particularly limited as long as it is a pharmaceutically acceptable salt, and examples thereof include salts with an inorganic acid such as hydrochloric acid, hydrobromic acid, hydroiodic acid, nitric acid, sulfuric acid or phosphoric acid; salts with an organic acid such as acetic acid, fumalic acid, maleic acid, succinic acid, citric acid, tartaric acid, adipic acid, gluconic acid, glucoheptonic acid, glucuronic acid, terephthalic acid, methanesulfonic acid, lactic acid, hippuric acid, 1,2-ethanedisulfonic acid, isethionic acid, lactobionic acid, oleic acid, pamoic acid, polygalacturonic acid, stearic acid, tannic acid, trifluoromethanesulfonic acid, benzenesulfonic acid, p-toluenesulfonic acid, lauryl sulfate, methyl sulfate, naphthalenesulfonic acid or sulfosalicylic acid; quaternary ammonium salts with methyl bromide, methyl iodide or the like; salts with a halogen ion such as a bromine ion, a chlorine ion or an iodine ion; salts with an alkali metal such as lithium, sodium or potassium; salts with an alkaline earth metal such as calcium or magnesium; salts with a metal such as iron or zinc; salts with ammonia; salts with an organic amine such as triethylenediamine, 2-aminoethanol, 2,2-iminobis(ethanol), 1-deoxy-1-(methylamino)-2-D-sorbitol,2-amino-2-(hydroxymethyl)-1,3-propanediol, procaine or N,N-bis(phenylmethyl)-1,2-ethanediamine, and the like.

In the case where there are geometrical isomers or optical isomers in the compound of the present invention, these isomers are also included in the scope of the present invention.

Further, the compound of the present invention may be in the form of a hydrate or a solvate.

Further, in the case where there is proton tautomerism in the compound of the present invention, the tautomeric isomers thereof are also included in the scope of the present invention.

(a) Preferred examples of the compound of the present invention include compounds in which the respective groups are as defined below in the compounds represented by the general formula (1) and salts thereof.

(a1) The ring X represents:

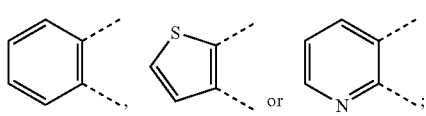

and/or (a2) $R^1$ represents an alkyl group, a cycloalkyl group, an aryl group, an aromatic heterocyclic group or a nonaromatic heterocyclic group; and/or (a3) in the case where $R^1$ is an alkyl group, the alkyl group may have one or plural substituents selected from a halogenoaryl group and an alkoxyaryl group; and/or (a4) in the case where $R^1$ is an aryl group, the aryl group may have one or plural substituents selected from a halogen atom, a hydroxy group, an alkoxy group, a halogenoalkoxy group, an alkyl group, a halogenoalkyl group, an alkynyl group, a cycloalkyl group, an amino group, an alkylamino group, an alkylthio group, an alkylcarbonyl group and a nitro group; and/or (a5) $R^2$ represents a hydrogen atom; and/or (a6) $R^1$ and $R^2$ may be combined together to form a nonaromatic heterocycle; and/or (a7) $R^3$ represents a quinolyl group, the quinolyl group may have one or plural substituents selected from a halogen atom, an alkoxy group and an alkyl group, and a nitrogen atom of the quinolyl group may be coordinated with an oxo ligand; and/or (a8) A represents a sulfur atom, a sulfinyl group or a sulfonyl group; and/or (a9) B represents an alkylene group.

That is, in the compounds represented by the general formula (1), preferred examples include compounds that comprises one or a combination of two or more selected from the above (a1), (a2), (a3), (a4), (a5), (a6), (a7), (a8) and (a9), and salts thereof.

(b) More preferred examples of the compound of the present invention include compounds in which the respective groups are as defined below in the compounds represented by the general formula (1) and salts thereof.

(b1) The ring X represents:

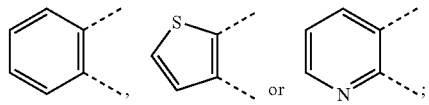

and/or (b2) $R^1$ represents a cycloalkyl group, an aryl group, an aromatic heterocyclic group or a nonaromatic heterocyclic group; and/or (b3) in the case where $R^1$ is an aryl group, the aryl group may have one or plural substituents selected from a halogen atom, a hydroxy group, an alkoxy group, a halogenoalkoxy group, an alkyl group, a halogenoalkyl group, an alkynyl group, a cycloalkyl group, an amino group, an alkylamino group, an alkylthio group, an alkylcarbonyl group and a nitro group; and/or (b4) $R^2$ represents a hydrogen atom; and/or (b5) $R^3$ represents a quinolyl group, the quinolyl group may have one or plural substituents selected from a halogen atom, an alkoxy group and an alkyl group, and a nitrogen atom of the quinolyl group may be coordinated with an oxo ligand; and/or (b6) A represents a sulfur atom or a sulfinyl group; and/or (b7) B represents an alkylene group.

That is, in the compounds represented by the general formula (1), more preferred examples include compounds that comprises one or a combination of two or more selected from the above (b1), (b2), (b3), (b4), (b5), (b6) and (b7), and salts thereof.

(c) Particularly preferred examples of the compound of the present invention include compounds in which the respective groups are as defined below in the compounds represented by the general formula (1) and salts thereof.

(c1) The ring X represents:

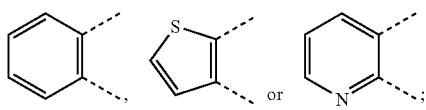

and/or (c2) R¹ represents a cyclohexyl group, a phenyl group, a 3-chlorophenyl group, a 4-chlorophenyl group, a 4-hydroxyphenyl group, a 4-isopropoxyphenyl group, a 4-trifluoromethoxyphenyl group, a 3-methylphenyl group, a 4-tert-butylphenyl group, a 3-ethynylphenyl group, a 4-cyclohexylphenyl group, a 3-aminophenyl group, a 4-dimethylaminophenyl group, a 3-methylthiophenyl group, a 4-methylcarbonylphenyl group, a 4-chloro-3-methylphenyl group, a 4-fluoro-3-methylphenyl group, a 3,5-dimethylphenyl group, a 4-isopropyl-3-methylphenyl group, a 4-nitro-3-trifluoromethylphenyl group, a 3,5-dimethyl-4-hydroxyphenyl group, an indan-5-yl group, a 1H-indazol-6-yl group, a 2,3-dihydroindol-5-yl group or an isoquinoline-3-yl group; and/or (c3) R² represents a hydrogen atom; and/or (c4) R³ represents a quinoline-3-yl group, a quinoline-4-yl group, a quinoline-6-yl group, a 7-bromoquinoline-4-yl group, a 6-methoxyquinoline-4-yl group, a 2-methylquinoline-4-yl group, a 6,7-dichloroquinoline-4-yl group, a 6,7-dimethoxyquinoline-4-yl group or a 1-oxoquinoline-4-yl group; and/or (c5) A represents a sulfur atom or a sulfinyl group; and/or (c6) B represents a methylene group or a methylmethylene group.

That is, in the compounds represented by the general formula (1), particularly preferred examples include compounds that comprises one or a combination of two or more selected from the above (c1), (c2), (c3), (c4), (c5) and (c6), and salts thereof.

(d) Particularly preferred specific examples of the compound of the present invention include compounds described below and salts thereof.

N-(4-Chlorophenyl)-2-(quinolin-4-ylmethylthio)pyridine-3-carboxamide
N-(3-Chlorophenyl)-2-(quinolin-4-ylmethylthio)pyridine-3-carboxamide
N-(3,5-Dimethylphenyl)-2-(quinolin-4-ylmethylthio)pyridine-3-carboxamide
N-(4-Fluoro-3-methylphenyl)-2-(quinolin-4-ylmethylthio) pyridine-3-carboxamide
N-(Indan-5-yl)-2-(quinolin-4-ylmethylthio)pyridine-3-carboxamide
N-(4-tert-Butylphenyl)-2-(quinolin-4-ylmethylthio)pyridine-3-carboxamide
N-(1H-Indazol-6-yl)-2-(quinolin-4-ylmethylthio)pyridine-3-carboxamide
N-(4-Isopropoxyphenyl)-2-(quinolin-4-ylmethylthio)pyridine-3-carboxamide
N-Phenyl-2-(quinolin-4-ylmethylthio)pyridine-3-carboxamide
N-(4-Dimethylaminophenyl)-2-(quinolin-4-ylmethylthio) pyridine-3-carboxamide
N-(4-Cyclohexylphenyl)-2-(quinolin-4-ylmethylthio)pyridine-3-carboxamide
N-(4-Methylcarbonylphenyl)-2-(quinolin-4-ylmethylthio)pyridine-3-carboxamide
N-(3-Ethynylphenyl)-2-(quinolin-4-ylmethylthio)pyridine-3-carboxamide
N-(4-Isopropyl-3-methylphenyl)-2-(quinolin-4-ylmethylthio)pyridine-3-carboxamide
N-(4-Hydroxyphenyl)-2-(quinolin-4-ylmethylthio)pyridine-3-carboxamide
N-(3-Methylthiophenyl)-2-(quinolin-4-ylmethylthio)pyridine-3-carboxamide
N-(3-Aminophenyl)-2-(quinolin-4-ylmethylthio)pyridine-3-carboxamide
N-(1-Acetyl-2,3-dihydroindol-5-yl)-2-(quinolin-4-ylmethylthio)pyridine-3-carboxamide
N-(4-Nitro-3-trifluoromethylphenyl)-2-(quinolin-4-ylmethylthio)pyridine-3-carboxamide
N-(3,5-Dimethyl-4-hydroxyphenyl)-2-(quinolin-4-ylmethyl thio)pyridine-3-carboxamide
N-Cyclohexyl-2-(quinolin-4-ylmethylthio)pyridine-3-carboxamide
N-(4-Chlorobenzyl)-2-(quinolin-4-ylmethylthio)pyridine-3-carboxamide
N-[2-(4-Methoxyphenyl)ethyl]-2-(quinolin-4-ylmethylthio)benzamide
N-(3,5-Dimethylphenyl)-2-[1-(quinolin-4-yl)ethylthio]pyridine-3-carboxamide
2-(6,7-Dimethoxyquinolin-4-ylmethylthio)-N-(3,5-dimethylphenyl)pyridine-3-carboxamide
N-(3-Chlorophenyl)-2-(6,7-dimethoxyquinolin-4-ylmethylthio)pyridine-3-carboxamide
2-(6,7-Dichloroquinolin-4-ylmethylthio)-N-(3,5-dimethyl phenyl)pyridine-3-carboxamide
2-(6,7-Dichloroquinolin-4-ylmethylthio)-N-(3-methylphenyl)pyridine-3-carboxamide
2-(7-Bromoquinolin-4-ylmethylthio)-N-(3,5-dimethylphenyl)pyridine-3-carboxamide
N-(3,5-Dimethylphenyl)-2-(1-oxoquinolin-4-ylmethylthio) pyridine-3-carboxamide
N-(3,5-Dimethylphenyl)-2-(quinolin-6-ylmethylthio)pyridine-3-carboxamide
N-(4-Chlorophenyl)-2-(quinolin-6-ylmethylthio)pyridine-3-carboxamide
N-(3-Chlorophenyl)-2-(quinolin-6-ylmethylthio)pyridine-3-carboxamide
N-(3,5-Dimethylphenyl)-2-(quinolin-3-ylmethylthio)pyridine-3-carboxamide
N-(3-Chlorophenyl)-2-(quinolin-3-ylmethylthio)pyridine-3-carboxamide
2-(Quinolin-4-ylmethylthio)-N-(4-trifluoromethoxyphenyl)pyridine-3-carboxamide
N-(3,5-Dimethylphenyl)-2-(quinolin-4-ylmethylthio)benzamide
N-(4-Chlorophenyl)-2-(quinolin-4-ylmethylthio)benzamide
2-(Quinolin-4-ylmethylthio)-N-(4-trifluoromethoxyphenyl)benzamide
N-(4-Chloro-3-methylphenyl)-2-(quinolin-4-ylmethylthio) benzamide
N-(4-tert-Butylphenyl)-2-(quinolin-4-ylmethylthio)benzamide
N-(3,5-Dimethylphenyl)-3-(quinolin-4-ylmethylthio) thiophene-2-carboxamide
N-(4-Chlorophenyl)-2-(6,7-dimethoxyquinolin-4-ylmethylthio)benzamide
N-(3,5-Dimethylphenyl)-2-(6-methoxyquinolin-4-ylmethylthio)pyridine-3-carboxamide
N-(3,5-Dimethylphenyl)-2-(2-methylquinolin-4-ylmethylthio)pyridine-3-carboxamide N-(3,5-Dimethylphenyl)-2-(quinolin-4-ylmethylsulfinyl)pyridine-3-carboxamide N-(Isoquinolin-3-yl)-2-(quinolin-4-ylmethylthio)pyridine-3-carboxamide The compounds of the present invention can be synthesized according to the following processes. Each specific process for synthesizing the present compounds is described in detail in later Examples (section of Production Examples). The term "Hal" used in the following synthetic routes represents a halogen atom and the "B" represents an alkylene group.

The synthetic routes for synthesizing the compounds of the present invention are divided roughly into the routes described below, and the suitable process can be chosen according to the kind of substituent.

Compound (I) of the present invention can be synthesized according to Synthetic Route 1. Namely, compound (I) can be obtained by reacting compound (II) with amine (III) in an organic solvent such as N,N-dimethylformamide, in the presence of a condensing agent such as O-(7-azabenzotriazol-1-yl)-1,1,3,3-tetramethyluronium hexafluorophosphate and a base such as N,N-diisopropylethylamine at room temperature to 50° C. for 1 hour to 24 hours.

Synthetic Route 1

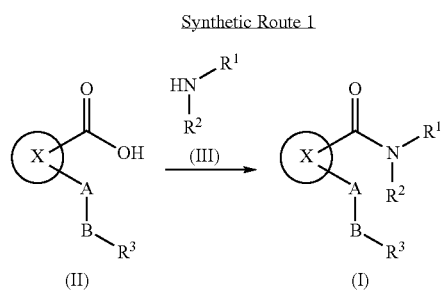

Compound (II) can be synthesized according to Synthetic Route 1-1. Namely, compound (II) can be obtained by reacting compound (IV) with compound (V) in an organic solvent such as N,N-dimethylformamide in the presence of a base such as triethylamine at 0° C. to room temperature for 1 hour to 24 hours.

Synthetic Route 1-1

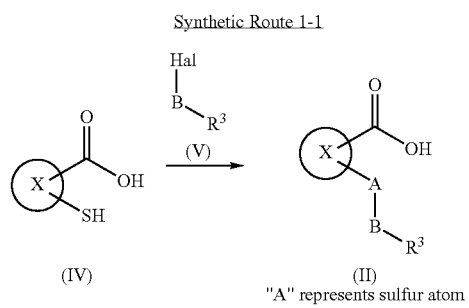
"A" represents sulfur atom

Compound (V) can be synthesized according to Synthetic Route 1-2. Namely, compound (V) can be obtained by reacting compound (VI) with a halogenation agent such as thionyl chloride in an organic solvent such as methylene chloride at 0° C. to room temperature for 1 hour to 3 hours.

Synthetic Route 1-2

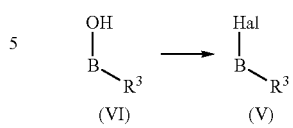

Compound (V) can also be synthesized according to Synthetic Route 1-3. Namely, compound (V) can be obtained by treating compound (VII) in an organic solvent such as benzene, in the presence of a radical initiator such as 2,2'-azobisisobutyronitrile and a halogenation reagent such as N-bromosuccinimide, under reflux for 1 hour to 12 hours.

Synthetic Route 1-3

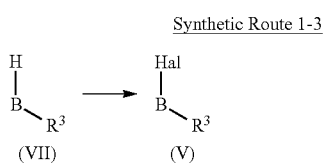

The compound (I) of the present invention can be synthesized according to Synthetic Route 2. Namely, compound (I) of this invention can be obtained by reacting compound (VIII) with compound (V) in an organic solvent such as N,N-dimethylformamide in the presence of a base such as triethylamine at 0° C. to room temperature for 1 hour to 24 hours.

Synthetic Route 2

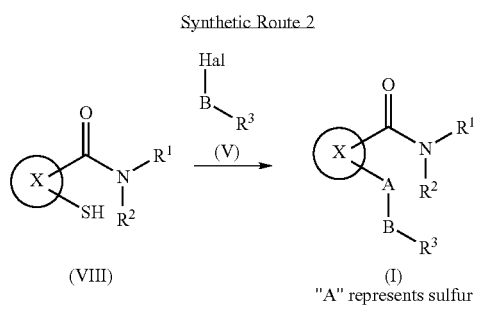
"A" represents sulfur

Compound (VIII) can be synthesized according to Synthetic Route 2-1. Namely, compound (VIII) can be obtained by reacting compound (IV) with amine (III) in an organic solvent such as N,N-dimethylformamide in the presence of a condensing reagent such as O-(7-azabenzotriazol-1-yl)-1,1,3,3-tetramethyluronium hexafluorophosphate and a base such as N,N-diisopropylethylamine at room temperature to 50° C. for 1 to 24 hours.

Synthetic Route 2-1

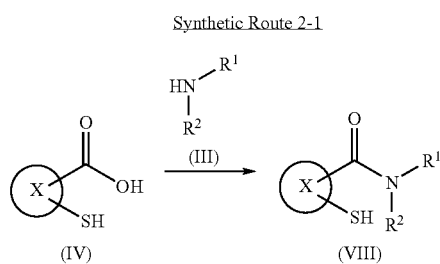

The compound (Ia) (p=0, 1 or 2, q=0 or 1) of the present invention, in which a sulfur atom or nitrogen atom is oxidized, can be synthesized according to Synthetic Route 3. Namely, the compound (Ia) of the present invention can be obtained by treating the compound (Ib) of the present invention in an organic solvent such as chloroform, in the presence of an oxidizing reagent such as m-chlorperbenzoic acid at 0° C. to room temperature for 1 hour to 24 hours. $R^4$ used in the synthetic route below represents one or plural substituents selected from a hydrogen atom, a halogen atom, an alkoxy group, an alkyl group and the like.

Synthetic Route 3

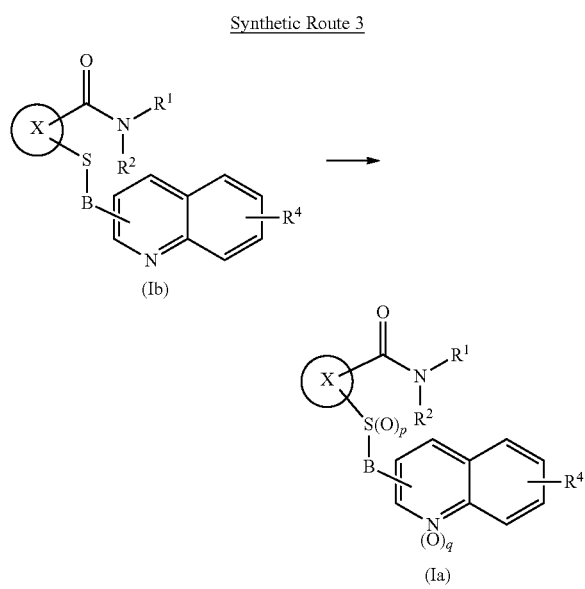

$R^4$ represents for one or plural (substituents such as a hydrogen atom, a halogen atom, an alkoxy group and an alkyl group.

The compound of the present invention prepared by the above synthetic routes can be converted into the above-mentioned salts, hydrate or solvate, using widely-used techniques.

In order to find the usefulness of the compound of the present invention, a test for inhibitory effects of the compound of the present invention on cell proliferation was carried out using a VEGF-induced HUVEC proliferation reaction evaluation system (HUVEC: human umbilical vein endothelial cells), which is a method of evaluating antiangiogenic effects of drugs, and the antiangiogenic effects of the compound were evaluated. As will be described in detail in the following Examples (in the section of Pharmacological Tests), it was found that the compounds of the present invention exhibit an excellent cell proliferation inhibitory action and have an antiangiogenic effect.

As described above, it has been reported that angiogenesis is deeply involved in diseases such as cancer, rheumatoid arthritis, age-related macular degeneration, diabetic retinopathy, retinopathy of prematurity, retinal vein occlusion, polypoid choroidal angiopathy, diabetic macular edema, psoriasis vulgaris and atherosclerosis. Therefore, the compound of the present invention is greatly expected to be used as a therapeutic agent for these diseases associated with angiogenesis.

The compound of the present invention can be administered orally or parenterally. Examples of the dosage form for administration include a tablet, a capsule, a granule, a powder, an injection, an ointment, an eye drop, an ophthalmic ointment and the like. Such a preparation can be prepared by a widely used technique.

For example, an oral preparation such as a tablet, a capsule, a granule or a powder can be prepared by optionally adding an excipient such as lactose, mannitol, starch, crystalline cellulose, light silicic anhydride, calcium carbonate or calcium hydrogen phosphate; a lubricant such as stearic acid, magnesium stearate or talc; a binder such as starch, hydroxypropyl cellulose, hydroxypropylmethyl cellulose or polyvinylpyrrolidone; a disintegrant such as carboxymethyl cellulose, low-substituted hydroxypropylmethyl cellulose or calcium citrate; a coating agent such as hydroxypropylmethyl cellulose, macrogol or a silicone resin; a stabilizer such as ethyl para-hydroxybenzoate or benzyl alcohol; a corrigent such as a sweetener, a sour agent or a flavor, or the like.

A parenteral preparation such as an injection or an eye drop can be prepared by optionally adding a tonicity agent such as sodium chloride, concentrated glycerin, propylene glycol, polyethylene glycol, potassium chloride, sorbitol or mannitol; a buffer such as sodium phosphate, sodium hydrogen phosphate, sodium acetate, citric acid, glacial acetic acid or trometamol; a surfactant such as polyoxyethylene sorbitan monooleate, polyoxyl 40 stearate or polyoxyethylene hydrogenated castor oil; a stabilizer such as sodium citrate or sodium edetate; a preservative such as benzalkonium chloride, paraben, benzethonium chloride, para-hydroxybenzoic acid ester, sodium benzoate or chlorobutanol; a pH adjusting agent such as hydrochloric acid, citric acid, phosphoric acid, glacial acetic acid, sodium hydroxide, sodium carbonate or sodium hydrogen carbonate; a soothing agent such as benzyl alcohol, or the like.

The present invention provides a method of treating a disease associated with angiogenesis comprising administering a therapeutically effective amount of the compound of the present invention to a patient.

The disease associated with angiogenesis is, for example, cancer, rheumatoid arthritis, age-related macular degeneration, diabetic retinopathy, retinopathy of prematurity, retinal vein occlusion, polypoid choroidal angiopathy, diabetic macular edema, psoriasis vulgaris, atherosclerosis or the like.

The dose of the compound of the present invention can be appropriately selected depending on the symptoms, age, dosage form or the like. For example, in the case of an oral preparation, it can be administered in an amount of generally 0.01 to 1,000 mg, preferably 1 to 100 mg per day in a single dose or several divided doses. Further, in the case of an eye drop, a preparation containing the compound of the present invention at a concentration of generally 0.0001 to 10% (w/v), preferably 0.01 to 5% (w/v) can be administered in a single dose or several divided doses.

PRODUCTION EXAMPLES

Reference Example 1

6,7-Dimethoxy-4-methylquinoline (Reference Compound No. 1-1)

The Reference Compound No. 1-1 was prepared following the method described in J. Org. Chem., 62, 568-577 (1997). Namely, iron (III) chloride hexahydrate (5.7 g, 21 mmol) and 3,4-dimethoxyaniline (3.1 g, 20 mmol) were added to acetic acid (60 mL), and then the mixture was stirred at 60° C. After all the solids were dissolved, methylvinylketone (1.8 mL, 22 mmol) was added dropwise for 5 minutes. Then the mixture was stirred at 140° C. for 1 hour, and allowed to cool down to room temperature, and the resulting solid was filtered off. Ethyl acetate (200 mL) was added to the solid, and the resulting organic solution was washed with 0.1N sodium hydroxide aqueous solution (200 mL) and brine (100 mL), and dried over anhydrous magnesium sulfate. The solvent was evaporated under reduced pressure, and the resulting solid was filtered off with diethyl ether to give 1.6 g of the title reference compound as a light brown solid (Yield: 38%).

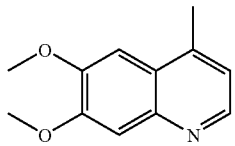

$^1$H-NMR (500 MHz,DMSO-$d_6$)

δ 2.63 (d,J=0.6 Hz,3H),3.92 (s,3H),3.94 (s,3H),7.19 (dd, J=4.4,0.6 Hz,1H),7.27 (s,1H),7.35 (s,1H),8.53 (d,J=4.4 Hz,1H)

As described below, Reference Compounds Nos. 1-2 to 1-3 were obtained following the method similar to that of Reference Compound No. 1-1, using the corresponding compounds selected from compounds which are on the market or compounds which are commonly known.

6,7-Dichloro-4-methylquinoline (Reference compound No. 1-2)

$^1$H-NMR (400 MHz,DMSO-$d_6$)

δ 2.69 (d,J=0.7 Hz,3H),7.47 (dd,J=4.4,0.7 Hz,1H),8.28 (s,1H),8.39 (s,1H),8.82 (d,J=4.4 Hz,1H)

7-Bromo-4-methylquinoline (Reference compound No. 1-3)

$^1$H-NMR (500 MHz,DMSO-$d_6$)

δ 2.69 (s,3H),7.43 (dd,J=4.3,0.9 Hz,1H),7.77 (dd,J=8.9, 2.1 Hz,1H),8.06 (d,J=8.9 Hz,1H),8.22 (m,1H),8.79 (d,J=4.3 Hz,1H)

Reference Example 2

6,7-Dichloro-4-formylquinoline (Reference compound No. 2-1)

Trifluoroacetic acid (360 μL, 4.7 mmol), tert-butyl iodide (450 μL, 3.8 mmol), iodine (990 mg, 3.9 mmol) and iron(II) chloride tetrahydrate (170 mg, 0.85 mmol) were added sequentially to a solution of 6,7-dichloro-4-methylquinoline (Reference compound No. 1-2, 790 mg, 3.7 mmol) in dimethylsulfoxide (18 mL) at room temperature, and the mixture was stirred at 80° C. for 7 hours. Then saturated sodium thiosulfate aqueous solution (100 mL) was added, and then ethyl acetate (300 mL) and saturated aqueous sodium hydrogencarbonate solution (200 mL) were added thereto. The mixture was separated into the organic layer and the aqueous layer, and the organic layer was washed with saturated brine (100 mL), dried over anhydrous magnesium sulfate, The solvent was evaporated under reduced pressure to give 840 mg of the title reference compound as a brown solid (Yield: 99%).

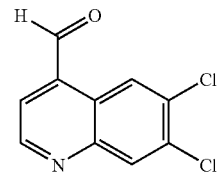

$^1$H-NMR (400 MHz,DMSO-$d_6$)

δ 8.14 (d,J=4.4 Hz,1H),8.47 (s,1H),9.20 (s,1H),9.30 (d,J=4.4 Hz,1H),10.49 (s,1H)

As described below, Reference Compounds Nos. 2-2 to 2-3 were obtained following the method similar to that of Reference Compound No. 2-1, using the corresponding compounds selected from Reference Compounds Nos. 1-1 to 1-3, compounds which are on the market or compounds which are commonly known.

6,7-Dimethoxy-4-formylquinoline (Reference Compound No. 2-2)

$^1$H-NMR (400 MHz,DMSO-$d_6$)

δ 3.97 (s,3H),3.97 (s,3H),7.53 (s,1H),7.87 (d,J=4.4 Hz,1H),8.36 (s,1H),9.00 (d,J=4.4 Hz,1H),10.51 (s,1H)

7-Bromo-4-formylquinoline (Reference Compound No. 2-3)

$^1$H-NMR (400 MHz,DMSO-$d_6$)

δ 7.97 (dd,J=9.0,2.0 Hz,1H),8.11 (d,J=4.2 Hz,1H),8.40 (d,J=2.0 Hz,1H),8.92 (d,J=9.0 Hz,1H),9.28 (d,J=4.2 Hz,1H), 10.51 (s,1H)

Reference Example 3

4-(Hydroxymethyl)quinoline (Reference Compound No. 3-1)

A solution of 4-quinolinecarboxylaldehyde (20 g, 130 mmol) in anhydrous tetrahydrofuran (200 mL) was added dropwise for 30 minutes to a suspension of sodium borohydride (5.3 g, 140 mmol) in anhydrous tetrahydrofuran (300 mL) under ice-cooling, and the mixture was stirred for 1 hour at room temperature. Water (300 mL) was added to the mixture, and the whole was then extracted with ethyl acetate (400 mL×once, 100 mL×three times) The organic layer was washed with brine (200 mL×3 times) and dried over anhydrous magnesium sulfate. The solvent was evaporated under reduced pressure, and the resulting solid was filtered off with diethyl ether and washed to give 14 g of the title Reference Compound as an orange-white solid (Yield: 69%)

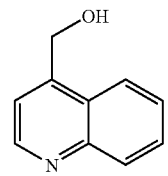

$^1$H-NMR (500 MHz,DMSO-$d_6$)

δ 5.04 (dd,J=5.5,0.9 Hz,2H),5.57 (t,J=5.5 Hz,1H),7.57-7.63 (m,2H),7.76 (m,1H),8.02-8.06 (m,2H),8.70 (d,J=4.3 Hz,1H)

As described below, Reference Compounds Nos. 3-2 to 3-7 were obtained following the method similar to that of Reference Compound No. 3-1, using the corresponding compounds selected from Reference Compounds Nos. 2-1 to 2-3, compounds which are on the market or compounds which are commonly known.

4-Hydroxymethyl-2-methylquinoline (Reference Compound No. 3-2)

$^1$H-NMR (400 MHz,DMSO-$d_6$)
δ 2.65 (s,3H),5.00 (dd,J=5.6,1.0 Hz,2H),5.54 (t,J=5.6 Hz,1H),7.46 (s,1H),7.52 (t,J=6.9 Hz,1H),7.69 (t,J=6.9 Hz,1H),7.92 (d,J=8.3 Hz,1H),7.98 (dd,J=8.3,1.0 Hz,1H)

6,7-Dimethoxy-4-(hydroxymethyl) quinoline (Reference Compound No. 3-3)

$^1$H-NMR (400 MHz,DMSO-$d_6$)
δ 3.92 (s,6H),4.96 (d,J=5.6 Hz,2H),5.51 (t,J=5.6 Hz,1H), 7.24 (s,1H),7.37 (s,1H),7.40 (d,J=4.4 Hz,1H),8.64 (d,J=4.4 Hz,1H)

6,7-Dichloro-4-(hydroxymethyl)quinoline (Reference Compound No. 3-4)

$^1$H-NMR (50 MHz,DMSO-$d_6$)
δ 5.01 (d,J=5.5 Hz,2H),5.67 (t,J=5.5 Hz,1H),7.64 (d,J=4.3 Hz,1H),8.31 (s,1H),8.36 (s,1H),8.93 (d,J=4.3 Hz,1H)

7-Bromo-4-(hydroxymethyl)quinoline (Reference Compound No. 3-5)

$^1$H-NMR (500 MHz,DMSO-$d_6$)
δ 5.03 (d,J=5.5 Hz,2H),5.63 (t,J=5.5 Hz,1H),7.62 (d,J=4.3 Hz,1H),7.76 (dd,J=8.9,2.1 Hz,1H),8.03 (d,J=8.9 Hz,1H), 8.24 (d,J=2.1 Hz,1H),8.90 (d,J=4.3 Hz,1H)

6-(Hydroxymethyl)quinoline (Reference Compound No. 3-6)

$^1$H-NMR (500 MHz,DMSO-$d_6$)
δ 4.70 (d,J=5.7 Hz,2H),5.42 (t,J=5.7 Hz,1H),7.51 (dd, J=8.3,4.2 Hz,1H),7.71 (dd,J=8.9,1.8 Hz,1H),7.89 (d,J=0.9 Hz,1H),7.98 (d,J=8.9 Hz,1H),8.35 (dd,J=8.3,1.5 Hz,1H), 8.86 (d,J=4.2,1.5 Hz,1H)

3-(Hydroxymethyl)quinoline (Reference Compound No. 3-7)

$^1$H-NMR (400 MHz,DMSO-$d_6$)
δ 4.73 (d,J=5.6 Hz,2H),5.47 (t,J=5.6 Hz,1H),7.60 (m,1H), 7.73 (m,1H),7.96-8.03 (m,2H),8.24 (m,1H),8.87 (d,J=2.2 Hz,1H)

Reference Example 4

4-(1-Hydroxyethyl)quinoline (Reference Compound No. 4-1)

Methyl magnesium bromide-1.0M dibutylether solution (7.0 mL, 7.0 mmol) was added dropwise for 5 minutes to a solution of 4-quinolinecarboxyaldehyde (510 mg, 3.2 mmol) in anhydrous tetrahydrofuran (10 mL) under ice-cooling, and the mixture was stirred under ice-cooling for 1.5 hours. Water (100 mL) was added thereto, and the whole was extracted with ethyl acetate (100 mL), the organic layer was washed with brine (100 mL) and dried over anhydrous magnesium sulfate. The solvent was evaporated under reduced pressure, and the resulting residue was purified by silica gel column chromatography to give 490 mg of the title reference compound as a white solid (Yield: 88%)

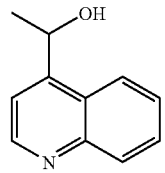

$^1$H-NMR (400 MHz,DMSO-$d_6$)
δ 1.47 (d,J=6.6 Hz,3H),5.52 (m,1H),5.56 (d,J=4.2 Hz,1H), 7.59-7.64 (m,2H),7.75 (m,1H),8.03 (dd,J=8.4,0.9 Hz,1H), 8.18 (dd,J=8.5,0.7 Hz,1H),8.88 (d,J=4.4 Hz,1H)

Reference Example 5

4-(Chloromethyl)quinoline (Reference Compound No. 5-1)

Thionyl chloride (12 mL, 170 mmol) was added dropwise for 15 minutes to a solution of 4-(hydroxymethyl)quinoline (Reference Compound No. 3-1, 13 g 82 mmol) in anhydrous dichloromethane (200 mL) under ice-cooling, and the mixture was stirred for 5 hours at room temperature. The solvent was evaporated under reduced pressure, and the resulting solid was filtered off with ethyl acetate, and washed to give 17 g of mixture containing the title Reference Compound, as a yellow-white solid.

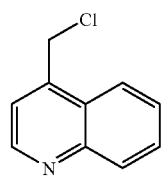

$^1$H-NMR (500 MHz,DMSO-$d_6$)
δ 5.44 (s,2H),7.90 (t,J=7.3 Hz,1H),7.97 (d,J=4.9 Hz,1H), 8.02 (m,1H),8.29 (d,J=8.6 Hz,1H),8.40 (d,J=8.2 Hz,1H),9.15 (d,J=4.9 Hz,1H)

As described below, Reference Compounds Nos. 5-2 to 5-8 were obtained following the method similar to that of Reference Compound No. 5-1, using the corresponding compounds selected from Reference Compounds Nos. 3-1 to 3-7, compounds which are on the market or compounds which are commonly known.

4-(1-Chloroethyl)quinoline (Reference Compound No. 5-2)

$^1$H-NMR (500 MHz,DMSO-$d_6$)
δ 1.99 (d,J=6.7 Hz,3H),6.34 (q,J=6.7 Hz,1H),7.91 (m,1H), 8.02-8.09 (m,2H),8.32 (d,J=8.6 Hz,1H),8.52 (d,J=8.2 Hz,1H),9.21 (d,J=5.2 Hz,1H)

4-Chloromethyl-6,7-dimethoxyquinoline (Reference Compound No. 5-3)

$^1$H-NMR (500 MHz,DMSO-$d_6$)
δ 4.02 (s,3H),4.04 (s,3H),5.47 (s,2H),7.66 (s,1H),7.70 (s,1H),7.90 (d,J=5.5 Hz,1H),8.97 (d,J=5.5 Hz,1H)

4-Chloromethyl-6,7-dichloroquinoline (Reference Compound No. 5-4)

¹H-NMR (400 MHz,DMSO-d₆)
δ 5.33 (s,2H),7.74 (d,J=4.3 Hz,1H),8.38 (s,1H),8.54 (s,1H),8.98 (d,J=4.3 Hz,1H)

7-Bromo-4-(chloromethyl)quinoline (Reference Compound No. 5-5)

¹H-NMR (500 MHz,DMSO-d₆)
δ 5.30 (s,2H),7.71 (d,J=4.3 Hz,1H),7.87 (dd,J=8.9,2.0 Hz,1H),8.20 (d,J=8.9 Hz,1H),8.30 (d,J=2.0 Hz,1H),8.94 (d,J=4.3 Hz,1H)

4-Chloromethyl-1-oxoquinoline (Reference Compound No. 5-6)

¹H-NMR (500 MHz,DMSO-d₆)
δ 5.27 (s,2H),7.63 (d,J=6.4 Hz,1H),7.83-7.90 (m,2H),8.28 (m,1H),8.58-8.62 (m,2H)

6-(Chloromethyl)quinoline (Reference Compound No. 5-7)

¹H-NMR (500 MHz,DMSO-d₆)
δ 4.98 (s,2H),7.57 (dd,J=8.6,4.2 Hz,1H),7.81 (dd,J=8.7, 2.0 Hz,1H),8.03-8.06 (m,2H),8.39 (dd,J=8.2,1.2 Hz,1H), 8.93 (dd,J=4.2,1.8 Hz,1H)

3-(Chloromethyl)quinoline (Reference Compound No. 5-8)

¹H-NMR (500 MHz,DMSO-d₆)
δ 5.09 (s,2H),7.82 (m,1H),7.98 (m,1H),8.18-8.24 (m,2H), 8.85 (d,J=6.7 Hz,1H),9.21 (m,1H)

Reference Example 6

4-Bromomethyl-6-methoxyquinoline (Reference Compound No. 6-1)

N-Bromosuccinimide (0.92 g, 5.2 mmol) and 2,2'-azobisisobutyronitrile (0.095 g, 0.58 mmol) were added to a solution of 6-methoxy-4-methylquinoline (1.0 g, 5.8 mmol) in anhydrous benzene (15 mL) at room temperature, and the mixture was stirred for 5 hours under reflux. Further 2,2'-azobisisobutyronitrile (0.19 g, 1.2 mmol) was added thereto, and the mixture was stirred for 17 hours under reflux. The solvent was evaporated under reduced pressure, and the resulting residue was roughly purified by silica gel chromatography to give 0.26 g of mixture containing the title Reference Compound as green oil.

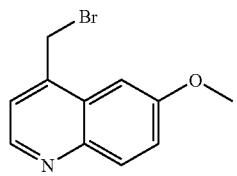

¹H-NMR (400 MHz,DMSO-d₆)
δ 3.96 (s,3H),5.20 (s,2H),7.44-7.62 (m,3H),7.99 (d,J=9.0 Hz,1H),8.71 (d,J=4.4 Hz,1H)

Reference Example 7

2-(Quinolin-4-ylmethylthio)pyridine-3-carboxylic acid (Reference Compound No. 7-1)

Triethylamine (33 mL, 240 mmol) was added to a suspension of a mixture containing 4-(chloromethyl) quinoline (Reference Compound No. 5-1, 17.0 g) and 2-mercaptonicotinic acid (13 g, 86 mmol) in anhydrous N,N-dimethylformamide (200 mL) at room temperature, and the mixture was stirred for 48 hours. Water (700 mL) and ethyl acetate (400 mL) were added thereto. After the mixture was separated into the organic layer and the aqueous layer, 1N hydrochloric acid (50 mL) was added to the aqueous layer. The precipitated solid was filtered off and dried under reduced pressure at 60° C. to give 15 g of the title Reference Compound as a yellow solid (Yield: 59%).

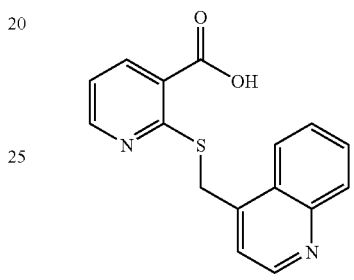

¹H-NMR (400 MHz,DMSO-d₆)
δ 4.90 (s,2H),7.30 (dd,J=7.6,4.9 Hz,1H), 7.63-7.68 (m,2H),7.78 (m,1H),8.05 (dd,J=8.5,0.7 Hz,1H),8.24-8.27 (m,2H),8.69 (dd,J=4.9,1.9 Hz,1H),8.80 (d,J=4.4 Hz,1H), 13.50 (s,1H)

As described below, Reference Compounds Nos. 7-2 to 7-10 were obtained following the method similar to that of Reference Compound No. 7-1, using the corresponding compounds selected from Reference Compounds Nos. 5-1 to 5-8, Reference Compound 6-1, compounds which are on the market or compounds which are commonly known.

3-(Quinolin-4-ylmethylthio)thiophene-2-carboxlic acid (Reference Compound No. 7-2)

¹H-NMR (400 MHz,DMSO-d₆)
δ 4.86 (s,2H),7.33 (d,J=5.4 Hz,1H),7.63 (d,J=4.4 Hz,1H), 7.68 (t,J=7.6 Hz,1H),7.80 (t,J=7.6 Hz,1H),7.90 (d,J=5.4 Hz,1H),8.06 (dd,J=7.6 Hz,1H),8.30 (d,J=7.6 Hz,1H),8.85 (d,J=4.4 Hz,1H),13.04 (br s,1H)

2-(Quinolin-4-ylmethylthio)benzoic acid (Reference Compound No. 7-3)

¹H-NMR (400 MHz,DMSO-d₆)
δ 4.75 (s,2H),7.26 (m,1H),7.50-7.58 (m,2H),7.62 (d,J=4.4 Hz,1H),7.69 (m,1H),7.80 (m,1H), 7.92 (m,1H), 8.07 (dd, J=8.5,0.7 Hz,1H),8.31 (dd,J=8.5,0.7 Hz,1H),8.85 (d,J=4.4 Hz,1H),13.10 (s,1H)

2-[1-(Quinolin-4-yl)ethylthio]pyridine-3-carboxylic acid (Reference Compound No. 7-4)

¹H-NMR (400 MHz,DMSO-d₆)
δ 1.79 (d,J=7.3 Hz,3H),6.12 (q,J=7.3 Hz,1H),7.14 (dd, J=7.5,6.0 Hz,1H),7.20 (dd,J=8.1,4.8 Hz,1H),7.94 (t,J=7.5

Hz,1H),8.06-8.34 (m,3H),8.52 (m,1H),8.63 (d,J=8.4 Hz,1H), 9.12 (d,J=5.5 Hz,1H),13.62 (br s,1H)

2-(6,7-Dimethoxyquinolin-4-ylmethylthio)pyridine-3-carboxlic acid (Reference Compound No. 7-5)

$^1$H-NMR (500 MHz,DMSO-d$_6$)
δ 3.86 (s,3H),3.96 (s,3H),4.96 (s,2H),7.30 (dd,J=7.6,4.7 Hz,1H),7.43 (s,1H),7.53-7.57 (m,2H), 8.26 (dd,J=7.6,1.8 Hz,1H),8.65-8.69 (m,2H),13.52 (s,1H)

2-(6,7-Dichloroquinolin-4-ylmethylthio)pyridine-3-carboxlic acid (Reference Compound No. 7-6)

$^1$H-NMR (400 MHz,DMSO-d$_6$)
δ 4.90 (s,2H),7.29 (dd,J=7.7,4.8 Hz,1H),7.72 (d,J=4.4 Hz,1H),8.25 (dd,J=7.7,1.8 Hz,1H),8.32 (s,1H),8.63 (s,1H), 8.66 (dd,J=4.8,1.8 Hz,1H),8.85 (d,J=4.4 Hz,1H),13.54 (s,1H)

2-(7-Bromoquinolin-4-ylmethylthio)pyridine-3-carboxlic acid (Reference No. 7-7)

$^1$H-NMR (400 MHz,DMSO-d$_6$)
δ 4.88 (s,2H),7.29 (dd,J=7.8,4.7 Hz,1H),7.69 (d,J=4.4 Hz,1H),7.81 (dd,J=9.0,2.0 Hz,1H),8.23-8.27 (m,3H),8.67 (dd,J=4.7,1.8 Hz,1H),8.83 (d,J=4.4 Hz,1H),13.52 (s,1H)

2-(1-Oxoquinolin-4-ylmethylthio)pyridine-3-carboxlic acid (Reference No. 7-8)

$^1$H-NMR (500 MHz,DMSO-d$_6$)
δ 4.85 (s,2H),7.30 (dd,J=7.9,4.8 Hz,1H),7.60 (d,J=6.4 Hz,1H),7.80 (m,1H),7.85 (m,1H),8.25 (dd,J=7.9,1.8 Hz,1H), 8.30 (dd,J=8.4,0.8 Hz,1H),8.51 (d,J=6.1 Hz,1H),8.59 (dd, J=8.7,1.1 Hz,1H),8.69 (dd,J=4.8,1.8 Hz,1H)

2-(Quinolin-6-ylmethylthio)pyridine-3-carboxlic acid (Reference Compound No. 7-9)

$^1$H-NMR (400 MHz,DMSO-d$_6$)
δ 4.58 (s,2H),7.27 (dd,J=7.8,4.6 Hz,1H),7.51 (dd,J=8.5, 4.4 Hz,1H),7.81 (dd,J=8.5,1.7 Hz,1H),7.96 (d,J=8.4 Hz,1H), 8.01 (d,J=1.7 Hz,1H),8.23 (dd,J=7.8,1.8 Hz,1H),8.32 (d,J=8.4 Hz,1H),8.69 (dd,J=4.6,1.8 Hz,1H),8.86 (dd,J=4.4, 1.7 Hz,1H),13.47 (s,1H)

2-(Quinolin-3-ylmethylthio)pyridine-3-carboxlic acid (Reference Compound No. 7-10)

$^1$H-NMR (500 MHz,DMSO-d$_6$)
δ 4.57 (s,2H),7.27 (dd,J=7.7,4.9 Hz,1H),7.58 (m,1H),7.72 (m,1H),7.94 (dd,J=8.3,1.2 Hz,1H),7.98 (dd,J=8.3,0.9 Hz,1H),8.22 (dd,J=7.7,1.8 Hz,1H),8.37 (d,J=1.8 Hz,1H), 8.69 (dd,J=4.9,1.8 Hz,1H),8.98 (d,J=2.1 Hz,1H),13.49 (br s,1H)

Reference Example 8

N-(4-Chlorophenyl)-2-mercaptopyridine-3-carboxamide (Reference Compound No. 8-1)

O-(7-Azabenzotriazol-1-yl)-N,N,N',N'-tetrauronium-hexafluorophosphate (5.4 g, 14 mmol) was added to a suspension of 2-mercaptonicotinic acid (2.0 g, 13 mmol), 4-chloroaniline (1.7 g, 13 mmol) and N,N-diisopropylethylamine (4.5 mL, 26 mmol) in anhydrous N,N-dimethylformamide (20 mL) at room temperature, and the mixture was stirred for 20 hours. Water (20 mL) was added thereto, the precipitated solid was filtered off, and washed with ethyl acetate. The resulting solid was dried at 40° C. under reduced pressure to give 2.0 g of the title Reference Compound as a yellow solid (Yield: 59%)

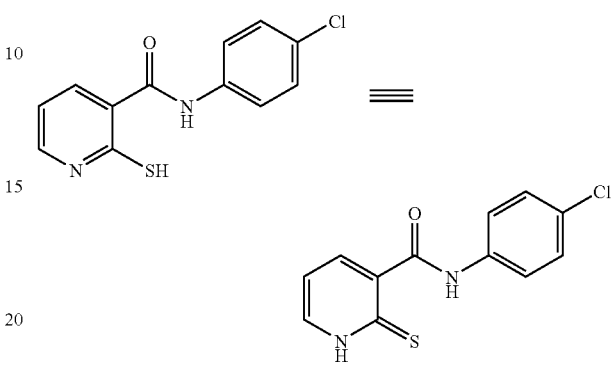

$^1$H-NMR (500 MHz,DMSO-d$_6$)
δ 7.08 (dd,J=7.6,6.0 Hz,1H),7.43 (d,J=8.9 Hz,2H),7.74 (d,J=8.9 Hz,2H),8.03 (dd,J=6.0,1.8 Hz,1H), 8.48 (dd,J=7.6, 1.8 Hz,1H),12.89 (s,1H),14.19 (s,1H)

As described below, Reference Compounds Nos. 8-2 to 8-11 were obtained following the method similar to that of Reference Compound No. 8-1, using the corresponding compounds selected from compounds which are on the market or compounds which are commonly known.

N-(3,5-Dimethylphenyl)-2-mercaptopyridine-3-carboxamide (Reference Compound No. 8-2)

$^1$H-NMR (400 MHz,DMSO-d$_6$)
δ 2.27 (s,6H),6.77 (s,1H),7.10 (dd,J=7.7,6.0 Hz,1H),7.35 (s,2H),8.03 (dd,J=6.0,2.0 Hz,1H),8.55 (dd,J=7.7,2.0 Hz,1H), 12.91 (s,1H),14.19 (s,1H)

2-Mercapto-N-(4-trifluoromethoxyphenyl)pyridine-3-carboxamide (Reference Compound No. 8-3)

$^1$H-NMR (400 MHz,DMSO-d$_6$)
δ 7.08 (dd,J=7.6,6.0 Hz,1H),7.39 (d,J=8.0 Hz,2H),7.82 (d,J 8.0 Hz,2H),8.03 (dd,J=6.0,2.0 Hz,1H),8.48 (dd,J=7.6,2.0 Hz,1H),12.90 (s,1H),14.19 (s,1H)

N-(4-Chlorophenyl)-2-mercaptobenzamide (Reference Compound No. 8-4)

$^1$H-NMR (500 MHz,DMSO-d$_6$)
δ 5.25 (br s,1H),7.25 (td,J=7.6,1.1 Hz,1H),7.36 (td,J=7.6, 1.4 Hz,1H),7.41 (dd,J=6.9,2.0 Hz,2H), 7.50 (dd,J=7.9,0.9 Hz,1H),7.62 (dd,J=7.8,1.4 Hz,1H),7.76 (dd,J=6.9,2.0 Hz,2H),10.53 (s,1H)

N-(3,5-Dimethylphenyl)-2-mercaptobenzamide (Reference Compound No. 8-5)

$^1$H-NMR (500 MHz,DMSO-d$_6$)
δ 2.26 (s,6H),5.25 (br s,1H),6.75 (s,1H),7.23 (m,1H),7.32-7.36 (m,3H),7.48 (d,J=7.9 Hz,1H),7.58 (d,J=7.6 Hz,1H), 10.23 (s,1H)

2-Mercapto-N-(4-trifluoromethoxyphenyl)benzamide (Reference Compound No. 8-6)

¹H-NMR (400 MHz,DMSO-d₆)
δ 5.27 (br s,1H),7.26 (td,J=7.4,1.2 Hz,1H),7.34-7.39 (m,3H),7.51 (dd,J=7.9,0.9 Hz,1H),7.63 (dd,J=7.6,1.5 Hz,1H),7.84 (dd,J=7.0,2.1 Hz,2H),10.61 (s,1H)

N-(4-Chloro-3-methylphenyl)-2-mercaptobenzamide (Reference Compound No. 8-7)

¹H-NMR (500 MHz,DMSO-d₆)
δ 2.33 (s,3H),5.25 (br s,1H),7.25 (td,J=7.6,1.1 Hz,1H) 7.34-7.39 (m,2H),7.50 (dd,J=7.9,0.9 Hz,1H),7.56 (dd,J=8.6, 2.4 Hz,1H),7.61 (dd,J=7.6,1.5 Hz,1H),7.75 (d,J=2.4 Hz,1H), 10.45 (s,1H)

N-(4-tert-Butylphenyl)-2-mercaptobenzamide (Reference Compound No. 8-8)

¹H-NMR (500 MHz,DMSO-d₆)
δ 1.28 (s,9H),5.25 (s,1H),7.24 (td,J=7.6,1.1 Hz,1H),7.32-7.38 (m,3H) 7.49 (dd,J=7.9,0.9 Hz,1H),7.60 (dd,J=7.8,1.4 Hz,1H),7.64 (d,J=8.6 Hz,2H),10.33 (s,1H)

N-(4-Chlorophenyl)-3-mercaptothiophene-2-carboxamide (Reference Compound No. 8-9)

¹H-NMR (400 MHz,DMSO-d₆)
δ 7.27 (br s,1H),7.41 (d,J=8.8 Hz,2H),7.73 (d,J=8.8 Hz,2H),7.85 (br s,1H),10.32 (s,1H)

N-(3,5-Dimethylphenyl)-3-mercaptothiophene-2-carboxamide (Reference Compound No. 8-10)

¹H-NMR (400 MHz,DMSO-d₆)
δ 2.27 (s,6H),6.77 (s,1H),7.26 (d,J=5.4 Hz,1H),7.32 (s,2H),7.82 (d,J=5.4 Hz,1H),10.04 (s,1H)

N-(Isoquinolin-3-yl)-2-mercaptopyridine-3-carboxamide (Reference Compound No. 8-11)

¹H-NMR (40 MHz,DMSO-d₆)
δ 7.15 (dd,J=7.8,6.1 Hz,1H),7.58 (t,J=7.5 Hz,1H),7.75 (t,J=7.0 Hz,1H),7.97 (d,J=8.1 Hz,1H),8.08-8.10 (m,2H), 8.69-8.72 (m,2H),9.19 (s,1H),13.71 (s,1H),14.24 (s,1H)

Example 1

N-(4-Chlorophenyl)-2-(quinolin-4-ylmethylthio) pyridine-3-carboxamide (Compound No. 1-1)

O-(7-Azabenzotriazol-1-yl)-N,N,N',N'-tetrauronium-hexafluorophosphate (140 mg, 0.38 mmol) was added to a solution of 2-(quinolin-4-ylmethylthio)pyridine-3-carboxylic acid (Reference Compound No. 7-1.91 mg, 0.31 mmol), 4-chloroaniline (52 mg, 0.40 mmol) and N,N-diisopropylethylamine (0.13 mL, 0.74 mmol) in anhydrous N,N-dimethylformamide (2.0 mL) at room temperature, and the mixture was stirred for 24 hours. Ethyl acetate (50 mL) was added thereto, and the whole was washed with saturated aqueous sodium hydrogencarbonate solution (50 mL, twice) and brine (50 mL), The organic layer was dried over anhydrous magnesium sulfate. The solvent was evaporated under reduced pressure, and then the precipitated solid was filtered off and washed with a mixture of diethyl ether and ethyl acetate (1:1). The resulting solid was dried at 50° C. under reduced pressure to give 93 mg of the target compound as a reddish-brown solid (Yield: 75%)

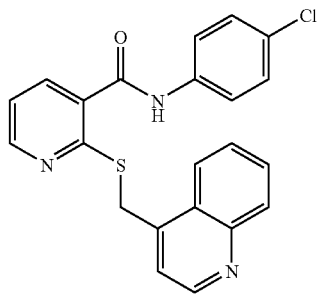

¹H-NMR (400 MHz,DMSO-d₆)
δ 4.94 (s,2H),7.32 (dd,J=7.6,4.9 Hz,1H),7.39 (dd,J=6.7, 2.1 Hz,2H),7.62-7.78 (m,5H),7.99-8.04 (m,2H),8.25 (dd, J=8.3,0.9 Hz,1H),8.65 (dd,J=4.9,1.5 Hz,1H),8.79 (d,J=4.3 Hz,1H), 10.58 (s,1H)

As described below, Compounds Nos. 1-2 to 1-40 were obtained following the method similar to that of Compound No. 1-1, using the corresponding compounds selected from Reference compounds Nos. 7-1 to 7-10, compounds which are on the market or compounds which are commonly known.

N-(3-Chlorophenyl)-2-(quinolin-4-ylmethylthio) pyridine-3-carboxamide (Compound No. 1-2)

¹H-NMR (400 MHz,DMSO-d₆)
δ 4.95 (s,2H),7.17 (m,1H),7.32-7.38 (m,2H),7.55 (d,J=8.1 Hz,1H),7.62-7.67 (m,2H), 7.75-7.79 (m,2H),8.00-8.04 (m,2H),8.26 (m,1H),8.66 (dd,J=4.9,1.7 Hz,1H),8.79 (d,J=4.2 Hz,1H),10.62 (s,1H)

N-(3,5-Dimethylphenyl)-2-(quinolin-4-ylmethylthio) pyridine-3-carboxamide (Compound No. 1-3)

¹H-NMR (500 MHz,DMSO-d₆)
δ 2.23 (s,6H),4.94 (s,2H),6.74 (s,1H),7.29-7.32 (m,3H), 7.62-7.66 (m,2H),7.77 (m,1H),7.95 (dd,J=7.6, 1.8 Hz,1H), 8.03 (d,J=7.6 Hz,1H),8.26 (dd,J=8.3,0.8 Hz,1H),8.63 (dd, J=4.9,1.8 Hz,1H),8.79 (d,J=4.6 Hz,1H),10.30 (s,1H)

N-(4-Fluoro-3-methylphenyl)-2-(quinolin-4-ylmethylthio)pyridine-3-carboxamide (Compound No. 1-4)

¹H-NMR (500 MHz,DMSO-d₆)
δ 2.20 (s,3H),4.94 (s,2H),7.09 (t,J=9.2 Hz,1H),7.32 (dd, J=7.6,4.9 Hz,1H),7.45 (m,1H), 7.59-7.66 (m,3H), 7.77 (m,1H),7.97 (dd,J=7.6,1.8 Hz,1H),8.03 (dd,J=8.2,0.9 Hz,1H),8.26 (dd,J=8.2,0.9 Hz,1H),8.64 (dd,J=4.9,1.8 Hz,1H),8.79 (d,J=4.3 Hz,1H),10.42 (s,1H)

N-(Indan-5-yl)-2-(quinolin-4-ylmethylthio)pyridine-3-carboxamide (Compound No. 1-5)

¹H-NMR (500 MHz,DMSO-d₆)
δ 1.98-2.02 (m,2H),2.78-2.84 (m,4H),4.94 (s,2H),7.15 (d,J=8.2 Hz,1H),7.29-7.35 (m,2H),7.58 (s,1H),7.62-7.66 (m,2H),7.77 (m,1H),7.95 (dd,J=7.7,1.5 Hz,1H),8.03 (dd, J=8.3,0.9 Hz,1H),8.26 (dd,J=8.3,0.9 Hz,1H),8.64 (d,J=1.5 Hz,1H),8.79 (d,J=4.3 Hz,1H),10.33 (s,1H)

N-(4-tert-Butylphenyl)-2-(quinolin-4-ylmethylthio) pyridine-3-carboxamide (Compound No. 1-6)

$^1$H-NMR (400 MHz,DMSO-d$_6$)
δ 1.25 (s,9H),4.94 (s,2H),7.29-7.34 (m,3H),7.56-7.66 (m,4H), 7.77 (m,1H),7.96 (m,1H),8.03 (d,J=8.5 Hz,1H),8.25 (d,J=8.3 Hz,1H),8.63 (dd,J=4.9,1.7 Hz,1H),8.79 (d,J=4.4 Hz,1H),10.38 (s,1H)

N-(1H-Indazol-6-yl)-2-(quinolin-4-ylmethylthio) pyridine-3-carboxamide (Compound No. 1-7)

$^1$H-NMR (400 MHz,DMSO-d$_6$)
δ 4.96 (s,2H),6.48 (m,1H),7.21 (m,1H),7.35 (m,1H),7.59-8.30 (m,8H),8.65 (dd,J=4.9,1.7 Hz,1H),8.79 (d,J=4.4 Hz,1H),10.60 (s,1H),12.94 (s,1H)

N-(4-Isopropoxyphenyl)-2-(quinolin-4-ylmethylthio) pyridine-3-carboxamide (Compound No. 1-8)

$^1$H-NMR (400 MHz,DMSO-d$_6$)
δ 1.23 (d,J=6.1 Hz,6H),4.54 (m,1H),4.93 (s,2H),6.87 (d,J=9.0 Hz,2H),7.30 (dd,J=7.6,4.9 Hz,1H), 7.54 (d,J=9.0 Hz,2H),7.62-7.66 (m,2H),7.77 (m,1H),7.95 (dd,J=7.6,1.7 Hz,1H),8.03 (dd,J=8.3,0.7 Hz,1H),8.25 (dd,J=8.3,0.7 Hz,1H),8.63 (dd,J=4.9,1.7 Hz,1H),8.79 (d,J=4.4 Hz,1H), 10.31 (s,1H)

N-Phenyl-2-(quinolin-4-ylmethylthio)pyridine-3-carboxamide (Compound No. 1-9)

$^1$H-NMR (400 MHz,DMSO-d$_6$)
δ 4.94 (s,2H),7.09 (m,1H),7.30-7.34 (m,3H),7.62-7.67 (m,4H), 7.77 (m,1H),7.99 (dd,J=7.6,1.7 Hz,1H),8.03 (dd,J=8.5,0.7 Hz,1H),8.26 (m,1H),8.64 (dd,J=4.9,1.7 Hz,1H), 8.79 (d,J=4.4 Hz,1H), 10.46 (s,1H)

N-(4-Dimethylaminophenyl)-2-(quinolin-4-ylmethylthio)pyridine-3-carboxamide (Compound No. 1-10)

$^1$H-NMR (500 MHz,DMSO-d$_6$)
δ 2.85 (s,6H),4.93 (s,2H),6.69 (d,J=9.2 Hz,2H),7.29 (dd,J=7.6,4.9 Hz,1H),7.47 (d,J=8.9 Hz,2H), 7.62-7.66 (m,2H),7.77 (m,1H),7.95 (dd,J=7.6,1.5 Hz,1H),8.03 (d,J=8.6 Hz,1H),8.26 (d,J=8.2 Hz,1H),8.62 (dd,J=4.9,1.5 Hz,1H), 8.79 (d,J=4.6 Hz,1H),10.16 (s,1H)

N-(4-Cyclohexylphenyl)-2-(quinolin-4-ylmethylthio) pyridine-3-carboxamide (Compound No. 1-11)

$^1$H-NMR (500 MHz,DMSO-d$_6$)
δ 1.19-1.38 (m,5H),1.67-1.78 (m,5H),2.46 (m,1H),4.93 (s,2H), 7.16 (d,J=8.6 Hz,2H),7.31 (dd,J=7.6,4.9 Hz,1H),7.55 (d,J=8.6 Hz,2H),7.61-7.66 (m,2H),7.77 (m,1H),7.96 (dd, J=7.6,1.5 Hz,1H), 8.03 (dd,J=8.5,0.7 Hz,1H),8.26 (dd,J=8.5, 0.7 Hz,1H),8.63 (dd,J=4.9,1.5 Hz,1H),8.79 (d,J=4.6 Hz,1H), 10.38 (s,1H)

N-(4-Methylcarbonylphenyl)-2-(quinolin-4-ylmethylthio)pyridine-3-carboxamide (Compound No. 1-12)

δ 2.55 (s,3H),4.94 (s,2H),7.32 (dd,J=7.6,4.9 Hz,1H),7.60-7.68 (m,2H),7.74-7.86 (m,3H),7.95 (dd,J=8.6 Hz,2H),8.02-8.08 (m,2H),8.25 (d,J=8.5 Hz,1H),8.67 (dd,J=4.9,1.6 Hz,1H),8.79 (d,J=4.4 Hz,1H),10.78 (s,1H)

N-(3-Ethynylphenyl)-2-(quinolin-4-ylmethylthio) pyridine-3-carboxamide (Compound No. 1-13)

$^1$H-NMR (400 MHz,DMSO-d$_6$)
δ 4.19 (s,1H),4.95 (s,2H),7.21 (d,J=7.8 Hz,1H),7.31-7.37 (m,2H), 7.62-7.67 (m,3H),7.77 (m,1H),7.84 (s,1H),7.99-8.05 (m,2H),8.26 (d,J=8.5 Hz,1H),8.65 (dd,J=4.9,1.7 Hz,1H),8.79 (d,J=4.4 Hz,1H),10.56 (s,1H)

N-(4-Isopropyl-3-methylphenyl)-2-(quinolin-4-ylmethylthio) pyridine-3-carboxamide (Compound No. 1-14)

$^1$H-NMR (400 MHz,DMSO-d$_6$)
δ 1.14 (d,J=6.8 Hz,6H),2.25 (s,3H),3.04 (m,1H),4.93 (s,2H),7.17 (d,J=8.3 Hz,1H),7.30 (dd,J=7.6,4.9 Hz,1H),7.40-7.43 (m,2H),7.62-7.67 (m,2H),7.77 (m,1H),7.94 (d,J=5.9 Hz,1H),8.03 (d,J=7.8 Hz,1H),8.26 (d,J=7.6 Hz,1H),8.63 (dd, J=4.9,1.7 Hz,1H),8.79 (d,J=4.4 Hz,1H),10.29 (s,1H)

N-(4-Hydroxyphenyl)-2-(quinolin-4-ylmethylthio) pyridine-3-carboxamide (Compound No. 1-15)

$^1$H-NMR (400 MHz,DMSO-d$_6$)
δ 4.93 (s,2H),6.70 (d,J=8.8 Hz,2H),7.29 (dd,J=7.6,4.9 Hz,1H) 7.44 (d,J=8.8 Hz,2H), 7.61-7.67 (m,2H),7.77 (m,1H),7.94 (dd,J=7.6,1.7 Hz,1H),8.03 (d,J=7.6 Hz,1H), 8.26 (d,J=7.6 Hz,1H),8.62 (dd,J=4.9,1.7 Hz,1H),8.79 (d,J=4.4 Hz,1H),9.26 (s,1H),10.21 (s,1H)

N-(3-Methylthiophenyl)-2-(quinolin-4-ylmethylthio) pyridine-3-carboxamide (Compound No. 1-16)

$^1$H-NMR (400 MHz,DMSO-d$_6$)
δ 2.44 (s,3H),4.94 (s,2H),6.99 (dq,J=7.9,0.9 Hz,1H),7.26 (t,J=7.9 Hz,1H),7.32 (dd,J=7.6,4.9 Hz,1H),7.42 (d,J=7.8 Hz,1H),7.62-7.67 (m,3H),7.77 (m,1H),7.99 (dd,J=7.6,1.7 Hz,1H),8.03 (dd,J=8.3,0.7 Hz,1H),8.26 (d,J=7.6 Hz,1H), 8.65 (dd,J=4.9,1.7 Hz,1H),8.79 (d,J=4.4 Hz,1H),10.47 (s,1H)

N-(3-Aminophenyl)-2-(quinolin-4-ylmethylthio) pyridine-3-carboxamide (Compound No. 1-17)

$^1$H-NMR (400 MHz,DMSO-d$_6$)
δ 4.93 (s,2H),5.10 (s,2H),6.29 (dd,J=7.8,1.2 Hz,1H),6.72 (d,J 7.8 Hz,1H),6.92 (t,J=7.9 Hz,1H), 7.01 (s,1H), 7.29 (dd, J=7.6,4.9 Hz,1H),7.62-7.67 (m,2H),7.77 (m,1H),7.91 (dd, J=7.6,1.8 Hz,1H), 8.03 (d,J=7.6 Hz,1H),8.26 (d,J=7.6 Hz,1H),8.62 (dd,J=4.9,1.8 Hz,1H),8.79 (d,J=4.4 Hz,1H), 10.15 (s,1H)

N-(1-Acetyl-2,3-dihydroindol-5-yl)-2-(quinolin-4-ylmethylthio)pyridine-3-carboxamide (Compound No. 1-18)

$^1$H-NMR (400 MHz,DMSO-d$_6$) δ 2.13 (s,3H),3.12 (t,J=8.4 Hz,2H),4.07 (t,J=8.4 Hz,2H),4.93 (s,2H),7.29-7.36 (m,2H), 7.61-7.67 (m,3H),7.77 (m,1H),7.94-7.98 (m,2H), 8.03 (dd,J=8.4,0.7 Hz,1H),8.26 (dd,J=8.4,0.7 Hz,1H), 8.63 (dd,J=4.9,1.7 Hz,1H),8.79 (d,J=4.4 Hz,1H),10.38 (s,1H)

N-(4-Nitro-3-trifluoromethylphenyl)-2-(quinolin-4-ylmethyl thio)pyridine-3-carboxamide (Compound No. 1-19)

$^1$H-NMR (400 MHz,CDCl$_3$)
δ 4.99 (s,2H),7.20 (dd,J=7.6,4.9 Hz,1H),7.47 (d,J=4.3 Hz,1H),7.61 (m,1H),7.73 (m,1H), 7.93-7.99 (m,3H),8.11 (dd,J=8.4,0.8 Hz,1H),8.16 (dd,J=8.4,0.8 Hz,1H),8.65 (dd,J=4.9,1.8 Hz,1H),8.68 (s,1H),8.74 (d,J=4.3 Hz,1H)

N-(3,5-Dimethyl-4-hydroxyphenyl)-2-(quinolin-4-ylmethylthio)pyridine-3-carboxamide (Compound No. 1-20)

$^1$H-NMR (400 MHz,DMSO-d$_6$)
δ 2.12 (s,6H),4.92 (s,2H),7.20 (s,2H),7.29 (dd,J=7.6,4.9 Hz,1H),7.61-7.67 (m,2H), 7.77 (m,1H), 7.92 (d,J=7.6 Hz,1H),8.03 (d,J=8.5 Hz,1H),8.08 (s,1H),8.26 (d,J=8.5 Hz,1H),8.61 (d,J=4.9 Hz,1H),8.79 (d,J=4.4 Hz,1H),10.08 (s,1H)

N-(2,2-Dimethylpropyl)-2-(quinolin-4-ylmethylthio)pyridine-3-carboxamide (Compound No. 1-21)

$^1$H-NMR (400 MHz,DMSO-d$_6$)
δ 0.86 (s,9H),3.01 (d,J=6.3 Hz,2H),4.90 (s,2H),7.24 (dd,J=7.6,4.9 Hz,1H),7.60 (d,J=4.4 Hz,1H), 7.65 (m,1H),7.75-7.80 (m,2H),8.03 (dd,J=8.4,0.9 Hz,1H),8.25 (dd,J=8.4,0.9 Hz,1H),8.42 (t,J=6.4 Hz,1H),8.57 (dd,J=4.9,1.7 Hz,1H),8.78 (d,J=4.4 Hz,1H)

N-Cyclohexyl-2-(quinolin-4-ylmethylthio)pyridine-3-carboxamide (Compound No. 1-22)

$^1$H-NMR (400 MHz,DMSO-d$_6$)
δ 1.07-1.31 (m,5H),1.53-1.79 (m,5H),3.64 (m,1H),4.89 (s,2H), 7.23 (dd,J=7.6,4.9 Hz,1H),7.61 (d,J=4.4 Hz,1H),7.65 (m,1H),7.75-7.80 (m,2H),8.04 (dd,J=8.5,0.7 Hz,1H),8.25 (dd,J=8.5,0.7 Hz,1H),8.33 (d,J=7.8 Hz,1H),8.56 (dd,J=4.9,1.7 Hz,1H),8.79 (d,J=4.4 Hz,1H)

N-(4-Chlorobenzyl)-2-(quinolin-4-ylmethylthio)pyridine-3-carboxamide (Compound No. 1-23)

$^1$H-NMR (400 MHz,DMSO-d$_6$)
δ 4.38 (d,J=5.9 Hz,2H),4.89 (s,2H),7.26 (dd,J=7.6,4.9 Hz,1H),7.31 (s,4H),7.60 (d,J=4.4 Hz,1H),7.66 (m,1H),7.79 (m,1H),7.89 (dd,J=7.6,1.7 Hz,1H),8.04 (d,J=7.8 Hz,1H), 8.25 (d,J=7.8 Hz,1H),8.60 (dd,J=4.9,1.7 Hz,1H),8.78 (d,J=4.4 Hz,1H),9.08 (t,J=5.9 Hz,1H)

N-(tert-Butyl)-2-(quinolin-4-ylmethylthio)benzamide (Compound No. 1-24)

$^1$H-NMR (400 MHz,DMSO-d$_6$)
δ 1.32 (s,9H),4.69 (s,2H),7.24 (m,1H),7.30-7.33 (m,2H),7.40 (d,J 7.8 Hz,1H),7.45 (d,J=4.4 Hz,1H), 7.64 (m,1H),7.77 (m,1H),7.84 (s,1H),8.03 (d,J=7.8 Hz,1H),8.30 (d,J=7.6 Hz,1H),8.77 (d,J=4.4 Hz,1H)

Morpholino-2-(quinolin-4-ylmethylthio)phenylmethanone (Compound No. 1-25)

$^1$H-NMR (400 MHz,DMSO-d$_6$)
δ 2.78 (s,2H),3.23 (s,2H),3.54 (s,4H),4.73 (s,2H),7.22 (dd,J=7.3,1.7 Hz,1H),7.29-7.37 (m,3H), 7.51 (dd,J=7.7,1.1 Hz,1H),7.65 (m,1H),7.77 (m,1H),8.02 (d,J=7.6 Hz,1H),8.27 (d,J=7.6 Hz,1H), 8.73 (d,J=4.4 Hz,1H)

N-[2-(4-Methoxyphenyl)ethyl]-2-(quinolin-4-ylmethylthio)benzamide (Compound No. 1-26)

$^1$H-NMR (400 MHz,DMSO-d$_6$)
δ 2.71 (t,J=7.4 Hz,2H),3.33-3.39 (m,2H),3.70 (s,3H),4.69 (s,2H),6.81 (d,J=8.5 Hz,2H),7.13 (d,J=8.5 Hz,2H),7.24 (m,1H),7.32-7.37 (m,2H),7.42-7.48 (m,2H),7.65 (m,1H), 7.77 (m,1H),8.03 (d,J=8.5 Hz,1H),8.28 (d,J=8.5 Hz,1H),8.39 (t,J=5.5 Hz,1H),8.77 (d,J=4.4 Hz,1H)

N-(2,2-Dimethylpropyl)-3-(quinolin-4-ylmethylthio)thiophene-2-carboxamide (Compound No. 1-27)

$^1$H-NMR (400 MHz,CDCl$_3$)
δ 0.77 (s,9H),2.83 (d,J=6.1 Hz,2H),4.41 (s,2H),6.87 (d,J=4.2 Hz,1H),6.91 (d,J=5.1 Hz,1H),7.41 (d,J=5.1 Hz,1H), 7.62 (m,1H),7.73-7.78 (m,2H),8.00 (d,J=8.3 Hz,1H),8.16 (d,J=8.3 Hz,1H),8.72 (d,J=4.2 Hz,1H)

N-[2-(4-Methoxyphenyl)ethyl]-3-(quinolin-4-ylmethylthio)thiophene-2-carboxamide (Compound No. 1-28)

$^1$H-NMR (400 MHz,CDCl$_3$)
δ 2.55 (t,J=7.1 Hz,2H),3.31 (td,J=7.1,5.9 Hz,2H),3.74 (s,3H),4.21 (s,2H),6.79-7.04 (m,4H),7.06 (d,J=8.5 Hz,2H), 7.36 (d,J 5.1 Hz,1H),7.60 (m,1H),7.72-7.77 (m,2H),7.93 (d,J=8.5 Hz,1H),8.14 (d,J=8.5 Hz,1H),8.70 (d,J=4.4 Hz,1H)

N-(3,5-Dimethylphenyl)-2-[1-(quinolin-4-yl)ethylthio]pyridine-3-carboxamide (Compound No. 1-29)

$^1$H-NMR (500 MHz,DMSO-d$_6$)
δ 1.79 (d,J=7.0 Hz,3H),2.23 (s,6H),6.04 (q,J=7.0 Hz,1H), 6.74 (s,1H), 7.27-7.30 (m,3H), 7.66 (m,1H), 7.70 (d,J=4.6 Hz,1H) 7.77 (m,1H) 7.93 (dd,J=7.6,1.5 Hz,1H),8.05 (dd,J=8.6,0.9 Hz,1H),8.28 (dd,J=8.6,0.9 Hz,1H),8.56 (dd,J=4.9,1.5 Hz,1H),8.85 (d,J=4.6 Hz,1H),10.31 (s,1H)

2-(6,7-Dimethoxyquinolin-4-ylmethylthio)-N-(3,5-dimethylphenyl)pyridine-3-carboxamide (Compound No. 1-30)

$^1$H-NMR (400 MHz,DMSO-d$_6$)
δ 2.23 (s,6H),3.82 (s,3H),3.92 (s,3H),4.92 (s,2H),6.74 (s,1H), 7.28 (s,2H), 7.31 (dd,J=7.6,4.9 Hz,1H), 7.37 (s,1H), 7.41 (d,J=4.6 Hz,1H),7.45 (s,1H),7.94 (dd,J=7.6,1.7 Hz,1H), 8.55 (d,J=4.6 Hz,1H), 8.65 (dd,J=4.9,1.7 Hz,1H),10.31 (s,1H)

N-(3-Chlorophenyl)-2-(6,7-dimethoxyquinolin-4-ylmethylthio)pyridine-3-carboxamide (Compound No. 1-31)

$^1$H-NMR (400 MHz,DMSO-d$_6$)
δ 3.83 (s,3H),3.92 (s,3H),4.94 (s,2H),7.17 (d,J=7.3 Hz,1H),7.32-7.56 (m,6H),7.86 (s,1H),8.01 (d,J=7.6 Hz,1H), 8.56 (d,J=4.6 Hz,1H),8.67 (dd,J=4.9,1.5 Hz,1H),10.65 (s,1H)

2-(6,7-Dichloroquinolin-4-ylmethylthio)-N-(3,5-dimethylphenyl)pyridine-3-carboxamide (Compound No. 1-32)

$^1$H-NMR (400 MHz,DMSO-$d_6$)

δ 2.24 (s,6H),4.93 (s,2H),6.75 (s,1H),7.29 (s,2H),7.31 (dd,J=7.6,4.9 Hz,1H),7.70 (d,J=4.4 Hz,1H), 7.96 (dd,J=7.6,1.7 Hz,1H),8.30 (s,1H),8.62 (dd,J 4.9,1.7 Hz,1H),8.64 (s,1H),8.84 (d,J=4.4 Hz,1H),10.30 (s,1H)

2-(6,7-Dichloroquinolin-4-ylmethylthio)-N-(3-methylphenyl)pyridine-3-carboxamide (Compound No. 1-33)

$^1$H-NMR (400 MHz,DMSO-$d_6$)

δ 2.28 (s,3H),4.94 (s,2H),6.92 (d,J=7.6 Hz,1H),7.21 (t,J=7.8 Hz,1H),7.32 (dd,J=7.6,4.9 Hz,1H),7.43 (d,J 8.1 Hz,1H),7.52 (s,1H),7.70 (d,J=4.4 Hz,1H),7.98 (dd,J=7.6,1.7 Hz,1H), 8.30 (s,1H),8.62 (dd,J=4.9,1.7 Hz,1H),8.64 (s,1H), 8.84 (d,J=4.4 Hz,1H),10.38 (s,1H)

2-(7-Bromoquinolin-4-ylmethylthio)-N-(3,5-dimethylphenyl)pyridine-3-carboxamide (Compound No. 1-34)

$^1$H-NMR (400 MHz,DMSO-$d_6$)

δ 2.23 (s,6H),4.92 (s,2H),6.74 (s,1H),7.28-7.33 (m,3H),7.67 (d,J 4.4 Hz,1H),7.79 (dd,J=8.9,2.1 Hz,1H),7.95 (dd,J=7.6,1.7 Hz,1H),8.23-8.27 (m,2H),8.62 (dd,J=4.9,1.7 Hz,1H),8.81 (d,J=4.4 Hz,1H),10.30 (s,1H)

N-(3,5-Dimethylphenyl)-2-(1-oxoquinolin-4-ylmethylthio)pyridine-3-carboxamide (Compound No. 1-35)

$^1$H-NMR (500 MHz,DMSO-$d_6$)

δ 2.23 (s,6H),4.88 (s,2H),6.74 (s,1H),7.28 (s,2H),7.31 (dd,J=7.6,4.9 Hz,1H),7.57 (d,J 6.4 Hz,1H),7.77 (m,1H),7.84 (m,1H),7.95 (dd,J=7.6,1.8 Hz,1H),8.30 (d,J=8.4,0.8 Hz,1H),8.49 (d,J=6.1 Hz,1H),8.58 (dd,J=8.7,1.1 Hz,1H),8.64 (dd,J=4.9,1.8 Hz,1H),10.28 (s,1H)

N-(3,5-Dimethylphenyl)-2-(quinolin-6-ylmethylthio)pyridine-3-carboxamide (Compound No. 1-36)

$^1$H-NMR (500 MHz,DMSO-$d_6$)

δ 2.24 (s,6H),4.62 (s,2H),6.74 (s,1H),7.28 (dd,J=7.6,4.9 Hz,1H),7.31 (s,2H),7.50 (dd,J=8.3,4.3 Hz,1H),7.79 (dd,J=8.7,2.0 Hz,1H),7.91 (dd,J=7.6,1.8 Hz,1H),7.94 (d,J=8.9 Hz,1H),7.99 (d,J=1.8 Hz,1H),8.30 (dd,J=8.3,1.1 Hz,1H),8.63 (dd,J=4.9,1.8 Hz,1H),8.85 (dd,J=4.3,1.8 Hz,1H), 10.30 (s,1H)

N-(4-Chlorophenyl)-2-(quinolin-6-ylmethylthio)pyridine-3-carboxamide (Compound No. 1-37)

$^1$H-NMR (400 MHz,DMSO-$d_6$)

δ 4.63 (s,2H),7.30 (dd,J=7.7,4.9 Hz,1H),7.40 (d,J=8.8 Hz,2H),7.52 (dd,J=8.3,4.4 Hz,1H),7.71 (d,J=8.8 Hz,2H),7.81 (dd,J=8.5,2.0 Hz,1H),7.93-8.01 (m,3H),8.33 (d,J=7.6 Hz,1H),8.65 (dd,J=4.9,1.7 Hz,1H),8.86 (dd,J=4.4,1.7 Hz,1H),10.59 (s,1H)

N-(3-Chlorophenyl)-2-(quinolin-6-ylmethylthio)pyridine-3-carboxamide (Compound No. 1-38)

$^1$H-NMR (400 MHz,DMSO-$d_6$)

δ 4.63 (s,2H),7.17 (ddd,J=7.8,2.0,0.9 Hz,1H),7.31 (dd,J=7.6,4.9 Hz,1H),7.37 (t,J=8.1 Hz,1H),7.52 (dd,J=8.5,4.4 Hz,1H),7.57 (d,J=8.3 Hz,1H),7.81 (dd,J=8.8,2.0 Hz,1H),7.88 (t,J=2.0 Hz,1H),7.93-8.01 (m,3H),8.33 (d,J=8.5 Hz,1H),8.66 (dd,J=4.9,1.7 Hz,1H),8.86 (dd,J=4.4,1.4 Hz,1H),10.64 (s,1H)

N-(3,5-Dimethylphenyl)-2-(quinolin-3-ylmethylthio)pyridine-3-carboxamide (Compound No. 1-39)

$^1$H-NMR (400 MHz,DMSO-$d_6$)

δ 2.24 (s,6H),4.61 (s,2H),6.75 (s,1H),7.27-7.30 (m,3H),7.58 (m, 1H),7.71 (m,1H),7.88-7.98 (m,3H),8.35 (d,J=1.7 Hz,1H),8.64 (dd,J=4.9,2.0 Hz,1H),8.95 (d,J=2.2 Hz,1H),10.29 (s,1H)

N-(3-Chlorophenyl)-2-(quinolin-3-ylmethylthio)pyridine-3-carboxamide (Compound No. 1-40)

$^1$H-NMR (500 MHz,DMSO-$d_6$)

δ 4.62 (s,2H),7.18 (dd,J=7.9,2.1,0.9 Hz,1H),7.31 (dd,J=7.6,4.9 Hz,1H),7.37 (t,J=8.1 Hz,1H), 7.54-7.60 (m,2H),7.71 (m,1H),7.87 (t,J=2.0 Hz,1H),7.92 (dd,J=8.4,1.1 Hz,1H),7.95-7.99 (m,2H),8.35 (d,J=1.8 Hz,1H),8.66 (dd,J=4.9,1.8 Hz,1H),8.96 (d,J=2.1 Hz,1H),10.62 (s,1H)

Example 2

2-(Quinolin-4-ylmethylthio)-N-(4-trifluoromethoxyphenyl)pyridine-3-carboxamide (Compound No. 2-1)

Triethylamine (66 μL, 0.47 mmol) was added to a solution of 2-mercapto-N-(4-trifluoromethoxyphenyl)pyridine-3-carboxamide (Reference Compound No. 8-3, 52 mg, 0.17 mmol) and 4-(chloromethyl)quinoline (Reference Compound No. 5-1, 28 mg, 0.16 mmol) in anhydrous N,N-dimethylformamide (11.0 mL) at room temperature, and the mixture was stirred for 18 hours. Ethyl acetate (50 mL) was added thereto, then the whole was washed with saturated aqueous sodium hydrogencarbonate solution (5 mL) and brine (50 mL). The organic layer was dried over anhydrous magnesium sulfate. The solvent was evaporated under reduced pressure, and then the resulting residue was purified by silica gel column chromatography to give 40 mg of the title compound as a white amorphous (Yield: 52%).

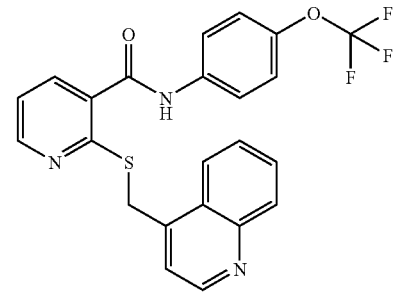

$^1$H-NMR (400 MHz,DMSO-$d_6$)

δ 4.95 (s,2H),7.31-7.38 (m,3H),7.61-7.68 (m,2H),7.74-7.80 (m, 3H),7.99-8.06 (m,2H),8.26 (d,J=8.3 Hz,1H),8.66 (dd,J=4.9,1.7 Hz,1H),8.79 (d,J=4.4 Hz,1H),10.66 (s,1H)

As described below, Compounds Nos. 2-2 to 2-12 were obtained following the method similar to that of Compound No. 2-1, using the corresponding compounds selected from Reference Compounds Nos. 5-1 to 5-8, Nos. 8-1 to 8-11, compounds which are on the market or compounds which are commonly known.

N-(3,5-Dimethylphenyl)-2-(quinolin-4-ylmethylthio) benzamide (Compound No. 2-2)

$^1$H-NMR (400 MHz,DMSO-$d_6$)
δ 2.24 (s,6H),4.73 (s,2H),6.73 (s,1H),7.33-7.35 (m,3H), 7.42 (m, 1H),7.47-7.51 (m,3H),7.56 (m,1H), 7.77 (m,1H), 8.02 (d,J=7.8 Hz,1H),8.27 (d,J=7.8 Hz,1H),8.77 (d,J=4.4 Hz,1H),10.22 (s,1H)

N-(4-Chlorophenyl)-2-(quinolin-4-ylmethylthio) benzamide (Compound No. 2-3)

$^1$H-NMR (500 MHz,DMSO-$d_6$)
δ 4.73 (s,2H),7.33-7.47 (m,5H),7.51-7.59 (m,3H),7.71-7.77 (m,3H),8.02 (dd,J=8.6,0.6 Hz,1H),8.26 (dd,J=8.6,0.6 Hz,1H),8.77 (d,J=4.6 Hz,1H),10.51 (s,1H)

2-(Quinolin-4-ylmethylthio)-N-(4-trifluoromethoxyphenyl)benzamide (Compound No. 2-4)

$^1$H-NMR (400 MHz,DMSO-$d_6$)
δ 4.73 (s,2H),7.33-7.38 (m,3H),7.42-7.48 (m,2H),7.52-7.58 (m,3H),7.74 (m,1H),7.80 (d,J=9.0 Hz,2H),8.01 (d,J=8.5 Hz,1H),8.25 (d,J=8.5 Hz,1H),8.77 (d,J=4.4 Hz,1H),10.58 (s,1H)

N-(4-Chloro-3-methylphenyl)-2-(quinolin-4-ylmethylthio)benzamide (Compound No. 2-5)

$^1$H-NMR (400 MHz,DMSO-$d_6$)
δ 2.30 (s,3H),4.73 (s,2H),7.32-7.37 (m,2H),7.40-7.48 (m,2H), 7.50-7.60 (m,4H),7.71-7.78 (m,2H),8.02 (d,J=7.8 Hz,1H),8.26 (d,J=7.8 Hz,1H),8.77 (d,J 4.2 Hz,1H),10.43 (s,1H)

N-(4-tert-Butylphenyl)-2-(quinolin-4-ylmethylthio) benzamide (Compound No. 2-6)

$^1$H-NMR (400 MHz,DMSO-$d_6$)
δ 1.27 (s,9H),4.73 (s,2H),7.32-7.36 (m,3H),7.43 (m,1H), 7.47-7.63 (m,6H),7.75 (m,1H),8.02 (d,J=7.6 Hz,1H),8.26 (d,J=7.6 Hz,1H),8.77 (d,J=4.2 Hz,1H),10.31 (s,1H)

N-(4-Chlorophenyl)-3-(quinolin-4-ylmethylthio) thiophene-2-carboxamide (Compound No. 2-7)

$^1$H-NMR (400 MHz,DMSO-$d_6$)
δ 4.77 (s,2H),7.30-7.38 (m,4H),7.50 (d,J=8.8 Hz,2H),7.60 (m,1H),7.74 (m,1H),7.89 (d,J=5.1 Hz,1H), 8.00 (m,1H),8.30 (m,1H),8.75 (d,J=4.4 Hz,1H),10.03 (br s,1H)

N-(3,5-Dimethylphenyl)-3-(quinolin-4-ylmethylthio) thiophene-2-carboxamide (Compound No. 2-8)

$^1$H-NMR (400 MHz,DMSO-$d_6$)
δ 2.21 (s,6H),4.76 (s,2H),6.70 (s,1H),7.01 (s,2H),7.29 (d,J=4.3 Hz,1H),7.36 (d,J=5.2 Hz,1H),7.63 (t,J=8.2 Hz,1H), 7.74 (t,J=8.2 Hz,1H),7.87 (d,J=5.2 Hz,1H),7.99 (d,J=8.2 Hz,1H),8.31 (d,J=8.2 Hz,1H),8.74 (d,J=4.3 Hz,1H),9.71 (s,1H)

N-(4-Chlorophenyl)-2-(6,7-dimethoxyquinolin-4-ylmethylthio)benzamide (Compound No. 2-9)

$^1$H-NMR (400 MHz,DMSO-$d_6$)
δ 3.85 (s,3H),3.91 (s,3H),4.68 (s,2H),7.27-7.55 (m,9H), 7.72 (d,J=8.8 Hz,2H),8.53 (d,J=4.4 Hz,1H),10.49 (s,1H)

N-(3,5-Dimethylphenyl)-2-(6-methoxyquinolin-4-ylmethylthio)pyridine-3-carboxamide (Compound No. 2-10)

$^1$H-NMR (400 MHz,DMSO-$d_6$)
δ 2.23 (s,6H),3.83 (s,3H),4.94 (s,2H),6.74 (s,1H),7.28-7.42 (m,4H),7.50 (d,J=2.7 Hz,1H),7.55 (d,J=4.4 Hz,1H), 7.92-7.96 (m,2H),8.62 (d,J=4.4 Hz,1H),8.65 (dd,J=4.9,1.7 Hz,1H),10.30 (s,1H)

N-(3,5-Dimethylphenyl)-2-(2-methylquinolin-4-ylmethylthio) pyridine-3-carboxamide (Compound No. 2-11)

$^1$H-NMR (500 MHz,CDCl$_3$)
δ 2.28 (s,6H),2.69 (s,3H),4.93 (s,2H),6.78 (s,1H),7.14 (s,2H), 7.17 (dd,J=7.6,4.9 Hz,1H),7.41 (s,1H),7.52 (td,J=7.6, 1.2 Hz,1H),7.68 (td,J=7.6,1.5 Hz,1H),7.73 (s,1H),7.92 (dd, J=7.6,1.5 Hz,1H),8.03 (d,J=7.6 Hz,1H),8.11 (dd,J=7.6,1.2 Hz,1H),8.60 (dd,J=4.9,1.8 Hz,1H)

N-(Isoquinolin-3-yl)-2-(quinolin-4-ylmethylthio) pyridine-3-carboxamide (Compound No. 2-12)

$^1$H-NMR (500 MHz,DMSO-$d_6$)
δ 4.96 (s,2H),7.31 (dd,J=7.6,4.9 Hz,1H),7.57 (m,1H),7.65 (m,1H),7.64 (d,J=4.3 Hz,1H), 7.71-7.78 (m,2H),7.94 (d,J=8.2 Hz,1H),8.04 (d,J=7.9 Hz,1H),8.07 (d,J=7.9 Hz,1H), 8.09 (d,J=7.6 Hz,1H),8.27 (d,J=7.6 Hz,1H),8.56 (s,1H),8.65 (dd,J=4.9,1.5 Hz,1H),8.80 (d,J=4.3 Hz,1H), 9.17 (s,1H), 11.16 (s,1H)

Example 3

N-(3,5-Dimethylphenyl)-2-(quinolin-4-ylmethylsulfinyl)pyridine-3-carboxamide (Compound No. 3-1)

m-Chloroperoxybenzoic acid (65%, 210 mg, 0.72 mmol) was added to a solution of N-(3,5-dimethylphenyl)-2-(quinolin-4-ylmethylthio)pyridine-3-carboxamide (Compound No. 1-3,200 mg, 0.50 mmol) in anhydrous dichloromethane (5.0 mL) under ice-cooling, and then the mixture was stirred at room temperature for 3 hours. The precipitated solid was filtered off with chloroform (30 mL) and 1N sodium hydroxide aqueous solution (30 mL), and washed. The resulting solid was dried at 50° C. under reduced pressure to give 150 mg of the target compound as a white solid (Yield: 70%).

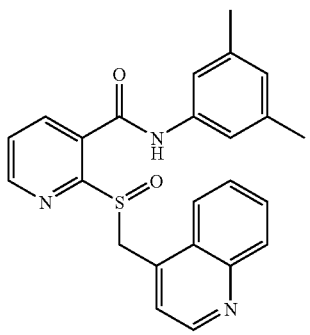

¹H-NMR (400 MHz,DMSO-d₆)

δ 2.31 (s,6H),4.65 (d,J=12.7 Hz,1H),5.06 (d,J=12.7 Hz,1H),6.82 (s,1H), 7.40-7.43 (m,3H), 7.53 (m,1H),7.72 (dd, J=7.8,4.6 Hz,1H),7.78 (m,1H),8.05 (d,J=7.8 Hz,1H),8.31 (dd,J=7.6,1.7 Hz,1H),8.40 (d,J=8.3 Hz,1H),8.81 (dd,J=4.6, 1.7 Hz,1H),8.85 (d,J=4.2 Hz,1H),10.69 (s,1H)

Example 4

N-(3,5-Dimethylphenyl)-2-(1-oxoquinolin-4-ylmethylsulfonyl)pyridine-3-carboxamide (Compound No. 4-1)

m-Chloroperoxybenzoic acid (65%, 280 mg, 1.0 mmol) was added to a suspension of N-(3,5-dimethylphenyl)-2-(quinolin-4-ylmethylsulfinyl)pyridine-3-carboxamide (Compound No. 3-1.92 mg, 0.22 mmol) in anhydrous dichloromethane (8.8 mL) at room temperature, and the mixture was stirred for 18 hours at room temperature. Chloroform (30 mL) and 1N sodium hydroxide aqueous solution (30 mL) were added thereto. The mixture was separated into the organic layer and the aqueous layer. The solid which precipitated in the aqueous layer was filtered off, and then washed with water (10 mL) and chloroform (10 mL). The resulting solid was dried at 50° C. under reduced pressure to give 100 mg of the target compound as a white solid (Yield: 99%).

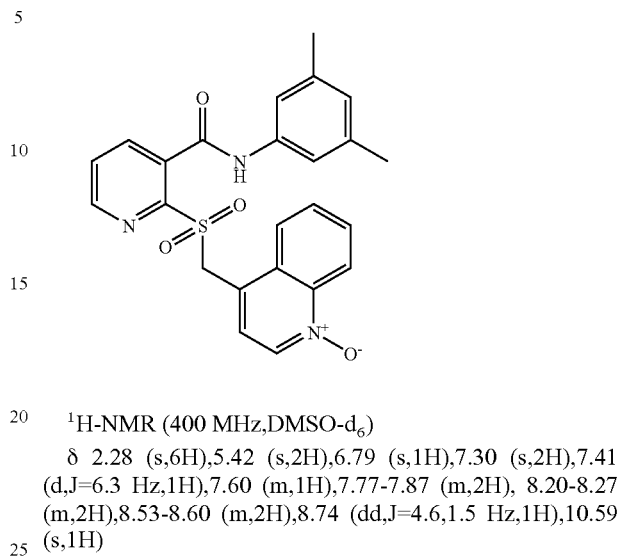

¹H-NMR (400 MHz,DMSO-d₆)

δ 2.28 (s,6H),5.42 (s,2H),6.79 (s,1H),7.30 (s,2H),7.41 (d,J=6.3 Hz,1H),7.60 (m,1H),7.77-7.87 (m,2H), 8.20-8.27 (m,2H),8.53-8.60 (m,2H),8.74 (dd,J=4.6,1.5 Hz,1H),10.59 (s,1H)

As shown above, the chemical structure of the compound of the present invention is shown below.

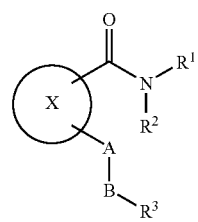

TABLE 1

| Compou | | A | B | R¹ | R² | R³ |
|---|---|---|---|---|---|---|
| 1-1 | ![pyridine carboxamide] | S | —CH₂— | ![4-chlorophenyl] | H | ![quinolin-4-yl] |
| 1-2 | ![pyridine carboxamide] | S | —CH₂— | ![3-chlorophenyl] | H | ![quinolin-4-yl] |

TABLE 1-continued

| Compou | [X-C(=O)-N structure] | A | B | R¹ | R² | R³ |
|---|---|---|---|---|---|---|
| 1-3 | nicotinamide | S | —CH₂— | 3,5-dimethylphenyl | H | quinolin-4-yl |
| 1-4 | nicotinamide | S | —CH₂— | 4-fluoro-3-methylphenyl | H | quinolin-4-yl |
| 1-5 | nicotinamide | S | —CH₂— | indan-5-yl | H | quinolin-4-yl |
| 1-6 | nicotinamide | S | —CH₂— | 4-tert-butylphenyl | H | quinolin-4-yl |
| 1-7 | nicotinamide | S | —CH₂— | 1H-indazol-6-yl | H | quinolin-4-yl |
| 1-8 | nicotinamide | S | —CH₂— | 4-isopropoxyphenyl | H | quinolin-4-yl |
| 1-9 | nicotinamide | S | —CH₂— | phenyl | H | quinolin-4-yl |
| 1-10 | nicotinamide | S | —CH₂— | 4-(dimethylamino)phenyl | H | quinolin-4-yl |

TABLE 2
| 1-11 | 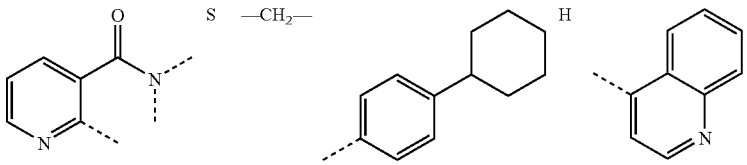 | S | —CH₂— | (4-cyclohexylphenyl) | H | (quinolin-4-yl) |
| --- | --- | --- | --- | --- | --- | --- |
| 1-12 | 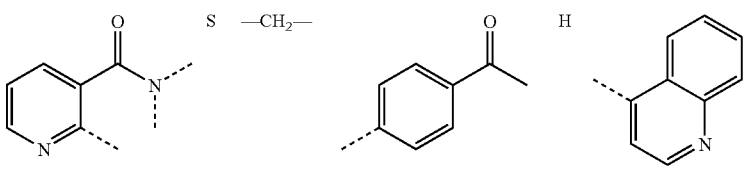 | S | —CH₂— | (4-acetylphenyl) | H | (quinolin-4-yl) |
| 1-13 | 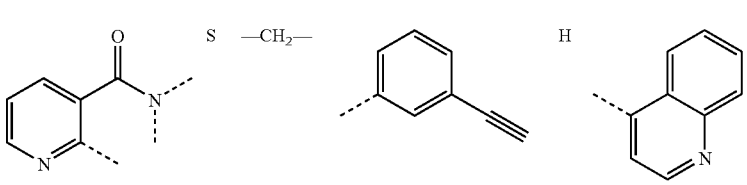 | S | —CH₂— | (3-ethynylphenyl) | H | (quinolin-4-yl) |
| 1-14 | 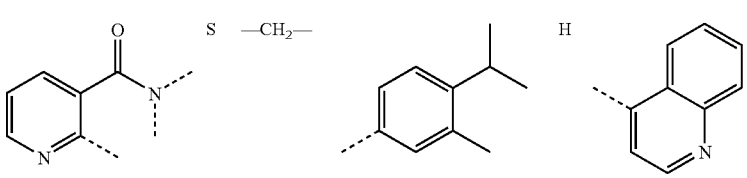 | S | —CH₂— | (4-isopropyl-3-methylphenyl) | H | (quinolin-4-yl) |
| 1-15 | 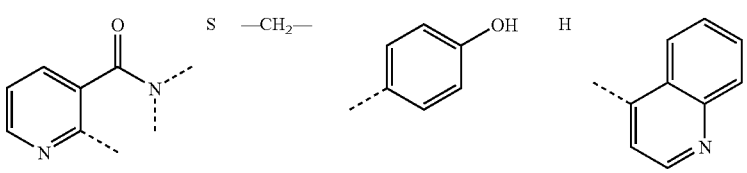 | S | —CH₂— | (4-hydroxyphenyl) | H | (quinolin-4-yl) |
| 1-16 | 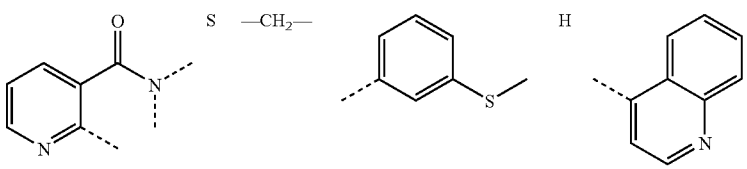 | S | —CH₂— | (3-methylthiophenyl) | H | (quinolin-4-yl) |
| 1-17 | 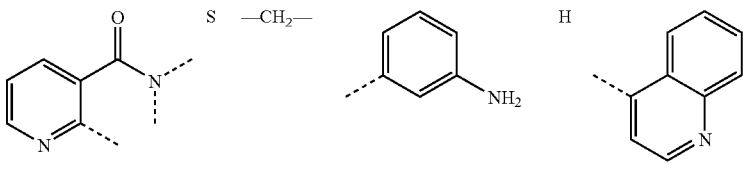 | S | —CH₂— | (3-aminophenyl) | H | (quinolin-4-yl) |
| 1-18 | 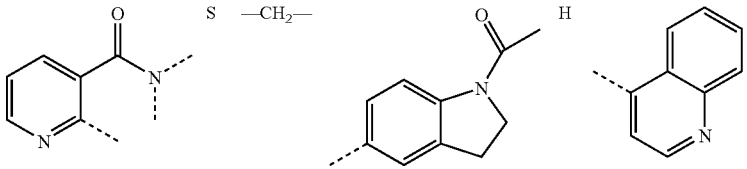 | S | —CH₂— | (1-acetyl-2,3-dihydro-1H-indol-5-yl) | H | (quinolin-4-yl) |
| 1-19 | 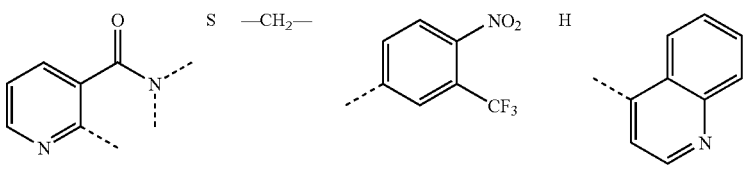 | S | —CH₂— | (4-nitro-3-trifluoromethylphenyl) | H | (quinolin-4-yl) |

TABLE 2-continued
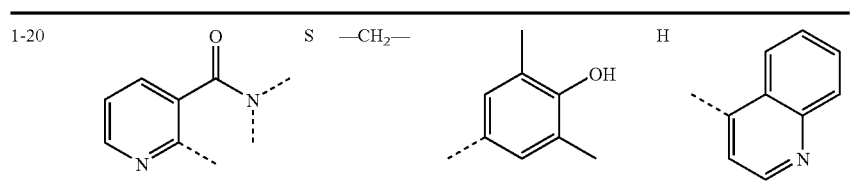
TABLE 3
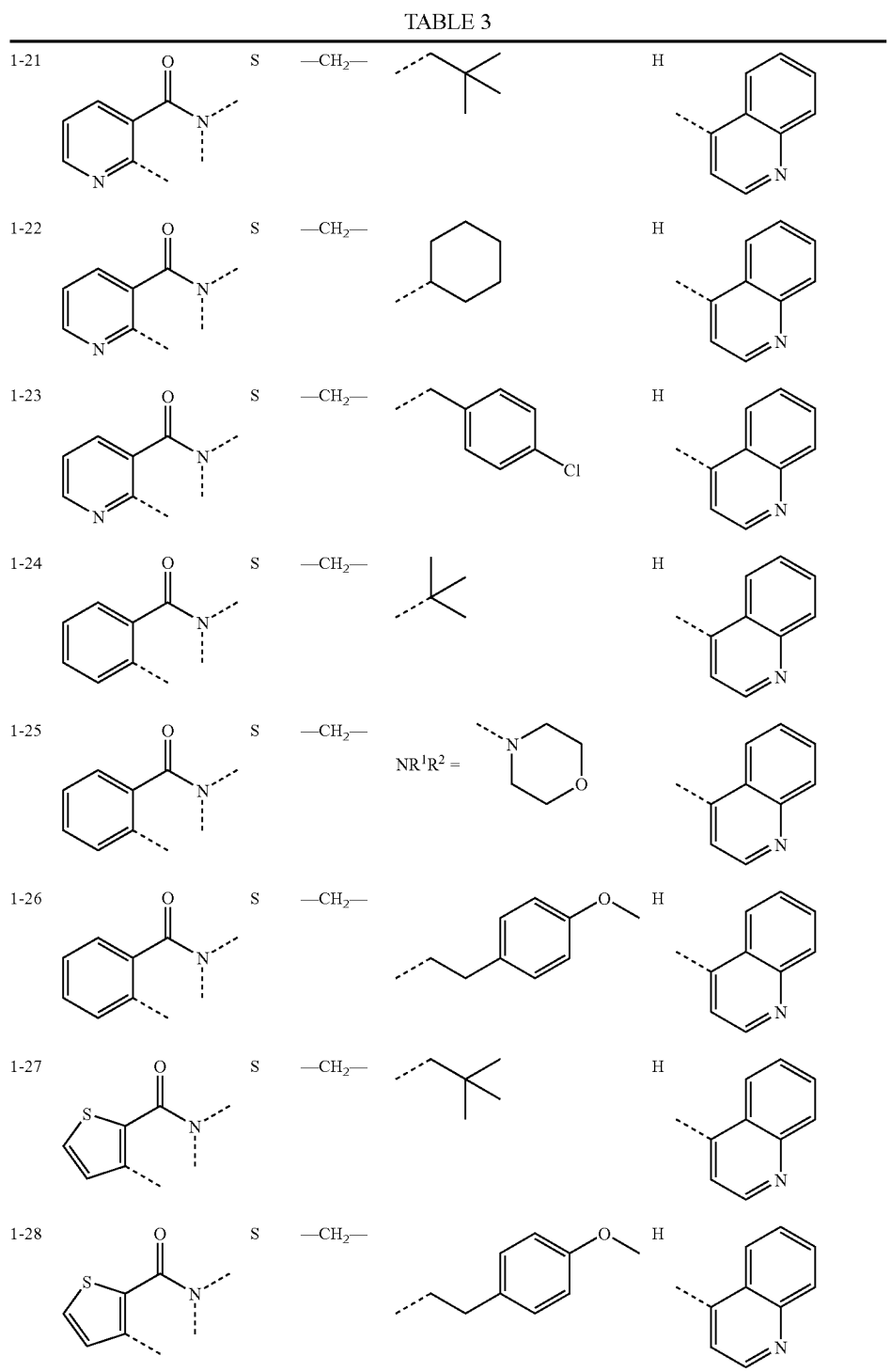

TABLE 3-continued
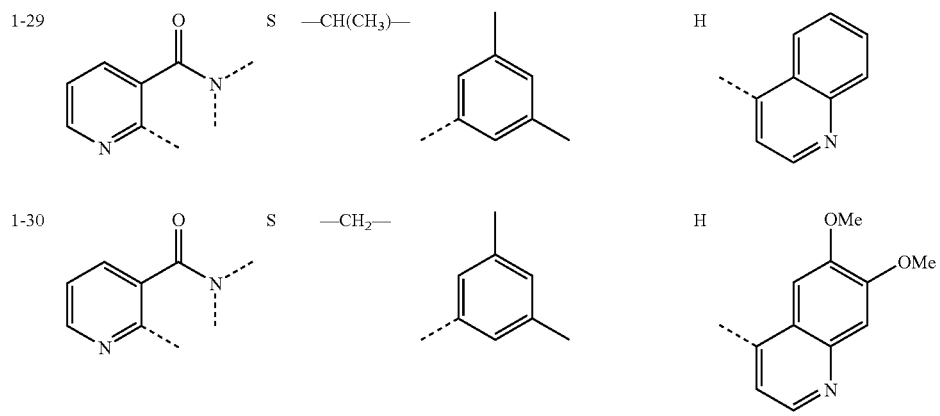
TABLE 4
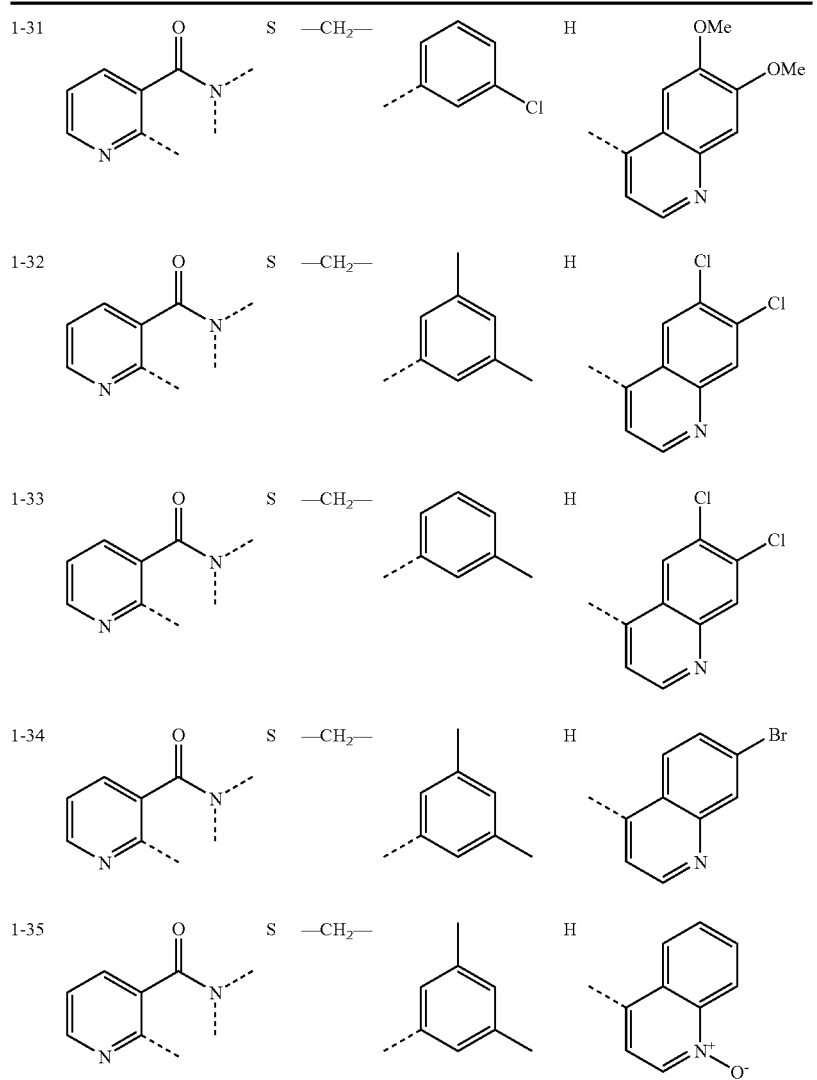

TABLE 4-continued
| 1-36 | 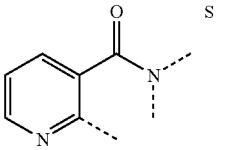 | S | —CH$_2$— | 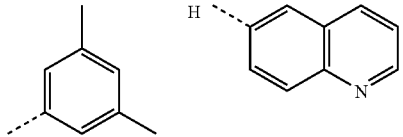 | H |  |
| 1-37 | 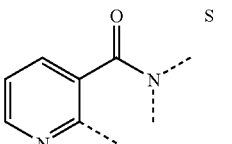 | S | —CH$_2$— | 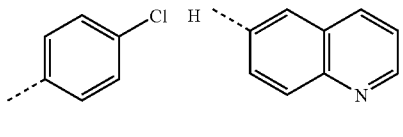 | H |  |
| 1-38 | 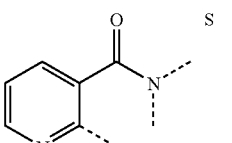 | S | —CH$_2$— | 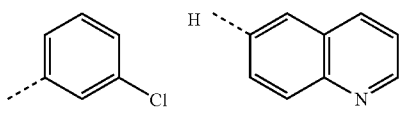 | H |  |
| 1-39 | 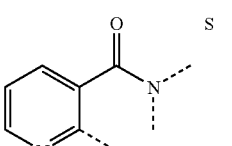 | S | —CH$_2$— | 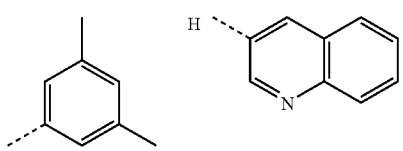 | H |  |
| 1-40 | 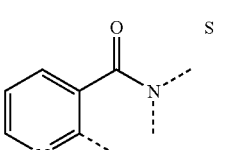 | S | —CH$_2$— | 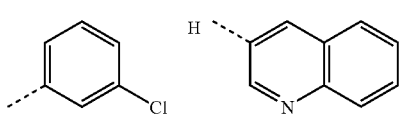 | H |  |
TABLE 5
| 2-1 | 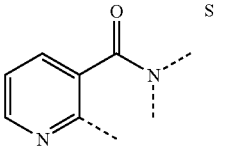 | S | —CH$_2$— | 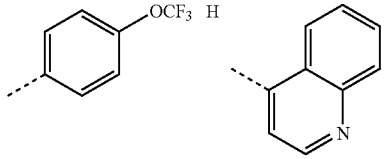 | H |  |
| 2-2 | 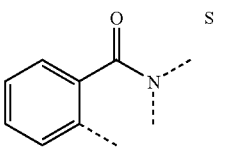 | S | —CH$_2$— | 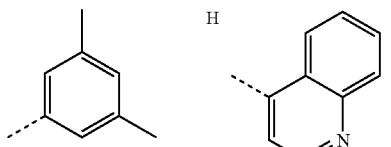 | H |  |
| 2-3 |  | S | —CH$_2$— | 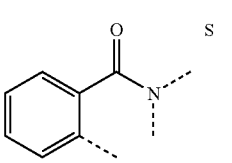 | H | 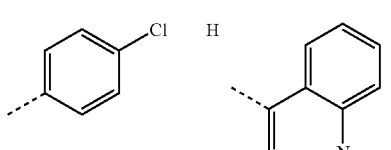 |
| 2-4 |  | S | —CH$_2$— | 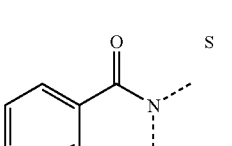 | H | 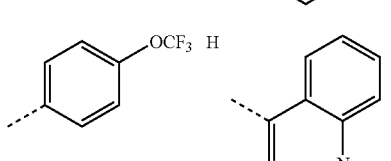 |

TABLE 5-continued

| 2-5 | [2-methylbenzamide, N-linked] | S | —CH₂— | [2-chloro-5-methylphenyl] | H | [quinolin-4-yl] |
| 2-6 | [benzamide, N-linked] | S | —CH₂— | [4-tert-butylphenyl] | H | [quinolin-4-yl] |
| 2-7 | [thiophene-2-carboxamide, 3-linked] | S | —CH₂— | [4-chlorophenyl] | H | [quinolin-4-yl] |
| 2-8 | [thiophene-2-carboxamide, 3-linked] | S | —CH₂— | [3,5-dimethylphenyl] | H | [quinolin-4-yl] |
| 2-9 | [benzamide, N-linked] | S | —CH₂— | [4-chlorophenyl] | H | [6,7-dimethoxyquinolin-4-yl] |
| 2-10 | [nicotinamide] | S | —CH₂— | [3,5-dimethylphenyl] | H | [6-methoxyquinolin-4-yl] |

TABLE 6

| 2-11 | [nicotinamide] | S | —CH₂— | [3,5-dimethylphenyl] | H | [2-methylquinolin-4-yl] |
| 2-12 | [nicotinamide] | S | —CH₂— | [4-trifluoromethoxyphenyl] | H | [quinolin-4-yl] |

TABLE 6-continued

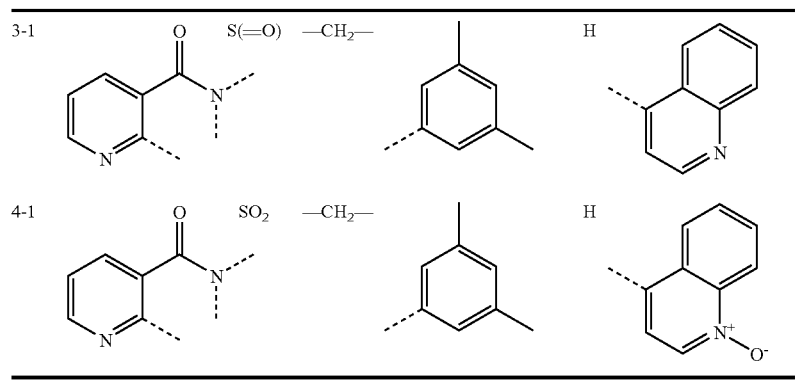

Preparation Examples

Hereinafter, typical preparation examples of the compound of the present invention are shown.

1) Tablet (in 100 mg)

| | |
|---|---|
| Compound of the present invention | 1 mg |
| Lactose | 66.4 mg |
| Cornstarch | 20 mg |
| Calcium carboxymethyl cellulose | 6 mg |
| Hydroxypropyl cellulose | 4 mg |
| Magnesium stearate | 0.6 mg |

The tablet of the above-mentioned formulation is coated using 2 mg of a coating agent (for example, a conventional coating agent such as hydroxypropylmethyl cellulose, macrogol or a silicone resin), whereby a desired coated tablet is obtained. In addition, a desired tablet can be obtained by appropriately changing the kinds and amounts of the compound of the present invention and additives.

2) Capsule

| Formulation 2 (in 150 mg) | |
|---|---|
| Compound of the present invention | 5 mg |
| Lactose | 145 mg |

A desired capsule can be obtained by appropriately changing the mixing ratio of the compound of the present invention to lactose.

3) Eye Drop

| Formulation 3 (in 100 mL) | |
|---|---|
| Compound of the present invention | 100 mg |
| Sodium chloride | 900 mg |
| Polysorbate 80 | 200 mg |
| Sodium hydroxide | q.s. |
| Hydrochloric acid | q.s. |
| Sterile purified water | q.s. |

A desired eye drop can be obtained by appropriately changing the kinds and amounts of the compound of the present invention and additives.

[Pharmacological Tests]

1. Evaluation Test for Antiangiogenic Effect

As one of the widely used methods of evaluating antiangiogenic effects of drugs, a cell proliferation inhibitory action test using a VEGF-induced HUVEC proliferation reaction evaluation system has been reported in Cancer Res., 59, 99-106 (1999). According to the method described in the above-mentioned document, a cell proliferation inhibitory action test of the compounds of the present invention was carried out, and the cell proliferation inhibition rate was calculated. Then, the antiangiogenic effect of each of the compounds of the present invention was evaluated using the obtained rate as an index.

(Preparation of Test Compound Solution)

Each test compound was dissolved in dimethyl sulfoxide (hereinafter abbreviated as DMSO), and the obtained solution was diluted with a commercially available phosphate buffer solution (hereinafter abbreviated as PBS), whereby a 20 μg/mL test compound solution was prepared.

(Preparation of HUVEC Suspension)

HUVEC was suspended in F12K medium containing 0.5% fetal bovine serum (hereinafter abbreviated as FBS), whereby a $2 \times 10^4$ cells/mL HUVEC suspension was prepared.

(Preparation of VEGF Solution)

VEGF was dissolved in PBS containing 0.1% bovine serum albumin, and the obtained solution was diluted with F12K medium containing 0.5% FBS, whereby a 400 ng/mL VEGF solution was prepared.

(Test Method and Measurement Method)

1) The HUVEC suspension was inoculated in an amount of 100 μL into each well of a 96-well plate coated with type I collagen ($2 \times 10^3$ cells per well).

2) One day after the inoculation, the test compound solution was added in an amount of 5 μL per well.

3) One hour after the addition of the test compound solution, the VEGF solution was added in an amount of 5 μL per well.

4) Three days after the addition of the VEGF solution, WST-8 assay reagent (Dojin Chemical Co., Ltd.) was added in an amount of 10 μL per well.

5) After 3 hours, the above-mentioned plate was attached to an absorptiometer (Multilabel Counter ARVO), and an absorbance at 450 nm of suspension in each well (hereinafter referred to as a test compound suspension) was measured.

6) A test was carried out in the same manner as in the above 1) to 5) except that 1.0% DMSO was used instead of the test compound solution. The result was used as a control.

Incubation was carried out under conditions of 37° C., 5% carbon dioxide and 95% oxygen in an incubator throughout the above-mentioned test steps.

(Calculation of Cell Proliferation Inhibition Rate)

The cell proliferation inhibition rate (%), which was used as an index of an antiangiogenic effect, was calculated using the following calculation equation.

(Calculation Equation)

Cell proliferation inhibition rate (%)=100−{(Absorbance of test compound suspension−A)/(absorbance of control−A)}×100

A: Absorbance of only cell suspension (cells+medium)

(Test Results and Discussion)

As an example of the test results, the cell proliferation inhibition rates (%) of the test compounds (Compound 1-1, Compound 1-3, Compound 1-26, Compound 1-30, Compound 1-31, Compound 1-33, Compound 1-35, Compound 1-36, Compound 1-38, Compound 1-39, Compound 2-1, Compound 2-2, Compound 2-3 and Compound 2-8 are shown in Table 7.

TABLE 7

| Compound | Cell proliferation inhibition rate (%) |
|---|---|
| 1-1 | 100 |
| 1-3 | 100 |
| 1-26 | 97 |
| 1-30 | 70 |
| 1-31 | 88 |
| 1-33 | 100 |
| 1-35 | 100 |
| 1-36 | 100 |
| 1-38 | 100 |
| 1-39 | 100 |
| 2-1 | 100 |
| 2-2 | 100 |
| 2-3 | 100 |
| 2-8 | 100 |

As shown in Table 7, the compounds of the present invention exhibited an excellent cell proliferation inhibitory action. Accordingly, the compounds of the present invention have an excellent antiangiogenic effect.

What is claimed is:

1. A compound represented by the following general formula (1) or a salt thereof:

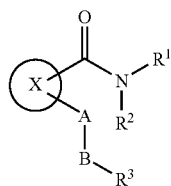

(1)

wherein the ring X represents

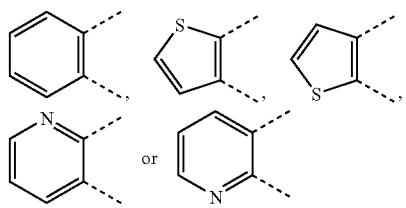

which may have one or plural substituents selected from a halogen atom and an alkyl group;

$R^1$ and $R^2$ may be the same or different and each represents a hydrogen atom, an alkyl group, a cycloalkyl group, an aryl group, an aromatic heterocyclic group or a nonaromatic heterocyclic group;

in the case where $R^1$ or $R^2$ is an alkyl group, the alkyl group may have one or plural substituents selected from an aryl group, a halogenoaryl group and an alkoxyaryl group;

in the case where $R^1$ or $R^2$ is an aryl group, the aryl group may have one or plural substituents selected from a halogen atom, a hydroxy group, an alkoxy group, a halogenoalkoxy group, an aryloxy group, an alkyl group, a halogenoalkyl group, an alkenyl group, an alkynyl group, a cycloalkyl group, an aryl group, an amino group, an alkylamino group, an arylamino group, a mercapto group, an alkylthio group, an arylthio group, an alkylcarbonyl group, an arylcarbonyl group and a nitro group;

$R^1$ and $R^2$ may be combined together to form a nonaromatic heterocycle;

$R^3$ represents a quinolyl group, the quinolyl group may have one or plural substituents selected from a halogen atom, a hydroxy group, an alkoxy group, an aryloxy group, an alkyl group and an aryl group, and a nitrogen atom of the quinolyl group may be coordinated with an oxo ligand;

A represents a sulfur atom, a sulfinyl group or a sulfonyl group; and

B represents an alkylene group.

2. The compound or a salt thereof according to claim 1, wherein in the general formula (1), the ring X represents:

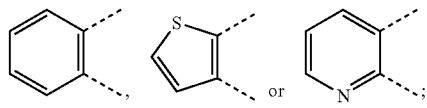

$R^1$ represents an alkyl group, a cycloalkyl group, an aryl group, an aromatic heterocyclic group or a nonaromatic heterocyclic group;

in the case where $R^1$ is an alkyl group, the alkyl group may have one or plural substituents selected from a halogenoaryl group and an alkoxyaryl group;

in the case where $R^1$ is an aryl group, the aryl group may have one or plural substituents selected from a halogen atom, a hydroxy group, an alkoxy group, a halogenoalkoxy group, an alkyl group, a halogenoalkyl group, an alkynyl group, a cycloalkyl group, an amino group, an alkylamino group, an alkylthio group, an alkylcarbonyl group and a nitro group;

$R^2$ represents a hydrogen atom;

R¹ and R² may be combined together to form a nonaromatic heterocycle;
R³ represents a quinolyl group, the quinolyl group may have one or plural substituents selected from a halogen atom, an alkoxy group and an alkyl group, and a nitrogen atom of the quinolyl group may be coordinated with an oxo ligand;
A represents a sulfur atom, a sulfinyl group or a sulfonyl group; and
B represents an alkylene group.

3. The compound or a salt thereof according to claim 1 or 2, wherein in the general formula (1),
the ring X represents:

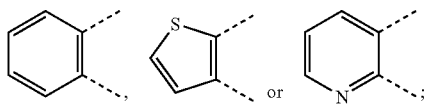

R¹ represents a cycloalkyl group, an aryl group, an aromatic heterocyclic group or a nonaromatic heterocyclic group;
in the case where R¹ is an aryl group, the aryl group may have one or plural substituents selected from a halogen atom, a hydroxy group, an alkoxy group, a halogenoalkoxy group, an alkyl group, a halogenoalkyl group, an alkynyl group, a cycloalkyl group, an amino group, an alkylamino group, an alkylthio group, an alkylcarbonyl group and a nitro group;
R² represents a hydrogen atom;
R³ represents a quinolyl group, the quinolyl group may have one or plural substituents selected from a halogen atom, an alkoxy group and an alkyl group, and a nitrogen atom of the quinolyl group may be coordinated with an oxo ligand;
A represents a sulfur atom or a sulfinyl group; and
B represents an alkylene group.

4. The compound or a salt thereof according to claim 1, wherein in the general formula (1),
the ring X represents:

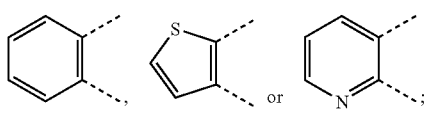

R¹ represents a cyclohexyl group, a phenyl group, a 3-chlorophenyl group, a 4-chlorophenyl group, a 4-hydroxyphenyl group, a 4-isopropoxyphenyl group, a 4-trifluoromethoxyphenyl group, a 3-methylphenyl group, a 4-tert-butylphenyl group, a 3-ethynylphenyl group, a 4-cyclohexylphenyl group, a 3-aminophenyl group, a 4-dimethylaminophenyl group, a 3-methylthiophenyl group, a 4-methylcarbonylphenyl group, a 4-chloro-3-methylphenyl group, a 4-fluoro-3-methylphenyl group, a 3,5-dimethylphenyl group, a 4-isopropyl-3-methylphenyl group, a 4-nitro-3-trifluoromethylphenyl group, a 3,5-dimethyl-4-hydroxyphenyl group, an indan-5-yl group, a 1H-indazol-6-yl group, a 2,3-dihydroindol-5-yl group or an isoquinoline-3-yl group;
R² represents a hydrogen atom;
R³ represents a quinoline-3-yl group, a quinoline-4-yl group, a quinoline-6-yl group, a 7-bromoquinoline-4-yl group, a 6-methoxy guinoline-4-yl group, a 2-methylquinoline-4-yl group, a 6,7-dichloro guinoline-4-yl group, a 6,7-dimethoxyquinoline-4-yl group or a 1-oxoquinoline-4-yl group;
A represents a sulfur atom or a sulfinyl group; and
B represents a methylene group or a methylmethylene group.

5. A compound selected from the group consisting of
N-(4-Chlorophenyl)-2-( guinolin-4-ylmethylthio)pyridine-3-carboxamide
N-(3-Chlorophenyl)-2-( guinolin-4-ylmethylthio)pyridine-3-carboxamide
N-(3,5-Dimethy lphenyl)-2-(quinolin-4-ylmethylthio)pyridine-3-carboxamide
N-(4-Fluoro-3- methylphenyl)-2-(quinolin-4-ylmethylthio)pyridine-3-carboxamide
N-(Indan-5-yl)-2-(quinolin-4-ylmethylthio)pyridine-3-carboxamide
N-(4-tert-Buty lphenyl)-2-(quinolin-4-ylmethylthio)pyridine-3-carboxamide
N-(1H-Indazol-6-yl)-2-(quinolin-4-ylmethylthio)pyridine-3-carboxamide
N-(4-Isopropoxyphenyl)-2-(quinolin-4-ylmethylthio)pyridine-3-carboxamide
N-Phenyl-2-(quino lin-4-ylmethylthio)pyridine-3-carboxamide
N-(4-Dimethylaminophenyl)-2-(quinolin-4-ylmethylthio)pyridine-3-carboxamide
N-(4-Cyclohexylphenyl)-2-(quinolin-4-ylmethylthio)pyridine-3-carboxamide
N-(4-Methylcarbonylphenyl)-2-(quinolin-4-ylmethylthio)pyridine-3-carboxamide
N-(3-Ethynylphenyl)-2-(quinolin-4-ylmethylthio)pyridine-3-carboxamide
N-(4-Isopropyl-3-methylphenyl)-2-(quinolin-4-ylmethylthio)pyridine-3-carboxamide N-(4-Hydroxyphenyl)-2-(quinolin-4-ylmethylthio)pyridine-3-carboxamide
N-(3-Methylthiophenyl)-2-(quinolin-4-ylmethylthio)pyridine-3-carboxamide
N-(3- Aminophenyl)-2-(quinolin-4-ylmethylthio)pyridine-3-carboxamide
N-(1-Acetyl-2,3-dihydroindol-5-yl)-2-(quinolin-4-ylmethy lthio)pyridine-3-carboxamide
N-(4-Nitro-3- trifluoromethylphenyl)-2-(quinolin-4-ylmethylthio)pyri(line-3-carboxamide
N-(3,5-Dimethyl-4-hydroxyphenyl)-2-(quinolin-4-ylmethylthio)pyridine-3-carboxamide
N-Cyclohexyl-2-(quinolin-4-ylmethylthio)pyridine-3-carboxamide
N-(4-Chlorobenzyl)-2-(quinolin-4-ylmethylthio)pyridine-3-carboxamide
N-[2-(4-Methoxyphenyl)ethyl]-2-(quinolin-4-ylmethylthio)benzamide
N-(3,5-Dimethylphenyl)-2-[1-(quinolin-4-yl)ethylthio]pyridine-3-carboxamide
2-(6,7-Dimethoxyquinolin-4-ylmethylthio)-N-(3, 5-dimethylphenyl)pyridine-3-carboxamide
N-(3-Chlorophenyl)-2-(6,7-dimethoxyquinolin-4-ylmethylthio)pyridine-3-carboxamide
2-(6,7-Dichloroquinolin-4-ylmethylthio)-N-(3,5-dimethy lphenyl)pyridine-3-carboxamide
2-(6,7-Dichloroquinolin-4-ylmethylthio)-N-(3-methylphenyl)pyridine-3-carboxamide
2-(7-Bromoquinolin-4-ylmethylthio)-N-(3,5-dimethylphenyl)pyridine-3-carboxamide
N-(3,5-Dimethylphenyl)-2-(1-oxoquinolin-4-ylmethylthio) pyridine-3-carboxamide N-(3,5-Dimethylphenyl)-2-(quinolin-6-ylmethylthio)pyridine-3-carboxamide
N-(4-Chlorophenyl)-2-(quinolin-6-ylmethylthio)pyridine-3-carboxamide
N-(3-Chlorophenyl)-2-(quinolin-6-ylmethylthio)pyridine-3-carboxamide
N-(3,5-Dimethylphenyl)-2-(quinolin-3-ylmethylthio)pyridine-3-carboxamide
N-(3-Chlorophenyl)-2-(quinolin-3-ylmethylthio)pyridine-3-carboxamide
2-(Quinolin-4-ylmethylthio)-N-(4-trifluoromethoxyphenyl)pyridine-3-carboxamide
N-(3,5-Dimethylphenyl)-2-(quinolin-4-ylmethylthio)benzamide
N-(4-Chlorophenyl)-2-(quinolin-4-ylmethylthio)benzamide
2-(Quinolin-4-ylmethylthio)-N-(4-trifluoromethoxyphenyl)benzamide
N-(4-Chloro-3-methylphenyl)-2-(quinolin-4-ylmethylthio)benzamide
N-(4-tert-Butylphenyl)-2-(quinolin-4-ylmethylthio)benzamide
N-(3,5-Dimethylphenyl)-3-(quinolin-4-ylmethylthio)thiophene-2-carboxamide
N-(4-Chlorophenyl)-2-(6,7-dimethoxyquinolin-4-ylmethylthio)benzamide
N-(3,5-Dimethylphenyl)-2-(6-methoxyquinolin-4-ylmethylthio)pyridine-3-carboxamide
N-(3,5-Dimethylphenyl)-2-(2-methylquinolin-4-ylmethylthio)pyridine-3-carboxamide
N-(3,5-Dimethylphenyl)-2-(quinolin-4-ylmethylsulfinyl)pyridine-3-carboxamide and
N-(Isoquinolin-3-yl)-2-(quinolin-4-ylmethylthio)pyridine-3-carboxamide or a salt thereof.

6. A pharmaceutical composition comprising the compound or a salt thereof according to claim 1 and a pharmaceutically acceptable carrier.

\* \* \* \* \*